United States Patent [19]

Okazaki et al.

[11] Patent Number: 4,569,943

[45] Date of Patent: Feb. 11, 1986

[54] PHYSIOLOGICALLY ACTIVE SUBSTANCE P-23924, ITS PRODUCTION AND USE

[75] Inventors: Hisayoshi Okazaki, Kyoto; Kazuhiko Ohta, Ikeda; Takenori Ishimaru, Toyonaka, all of Japan

[73] Assignee: Takeda Chemical Industries, Ltd., Osaka, Japan

[21] Appl. No.: 543,943

[22] Filed: Oct. 19, 1983

[30] Foreign Application Priority Data

Oct. 20, 1982 [JP] Japan ................................ 57-185043
Aug. 2, 1983 [JP] Japan ................................ 58-142347

[51] Int. Cl.4 .................... C07C 50/16; C07C 147/107
[52] U.S. Cl. ............................. 514/562; 260/396 R; 567/427; 568/637; 514/682; 514/721; 514/756
[58] Field of Search ............... 260/396 K; 562/427; 568/632; 514/562, 682, 721, 756

[56] References Cited

PUBLICATIONS

*Chemical Abstracts*, vol. 85, No. 46, 287g, Kurt, "Die-1-Alde Reaction of Thiophene Oxides Generated in Situ," 1976.

*Chemical Abstracts*, vol. 101, No. 116,580x, Hocquaux, "5-Hydroxy-1,4-Naphthaquinone Dye for Keratin Fibers, Especially Hair," 1984.

*Primary Examiner*—Richard L. Raymond
*Assistant Examiner*—Raymond Covington
*Attorney, Agent, or Firm*—Wenderoth, Lind & Ponack

[57] ABSTRACT

The compound of the formula:

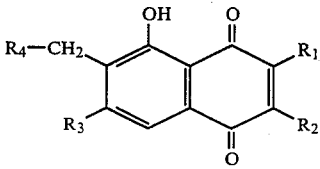

wherein $R_1$ is hydrogen, methyl or hydroxymethyl, $R_2$ is hydrogen or methoxy, $R_3$ is hydroxy or methoxy, and $R_4$ is hydrogen or a group

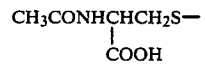

is novel, and the compound is of use as inhibitors of animal tissue fibrosis, or biochemical reagents.

14 Claims, 30 Drawing Figures

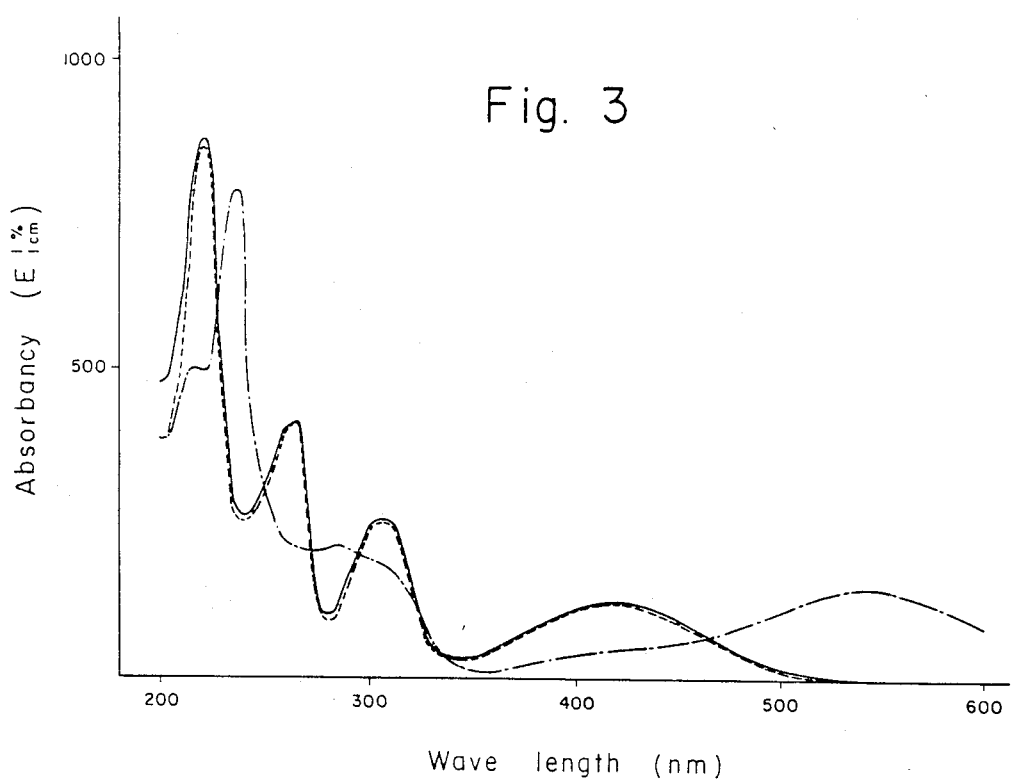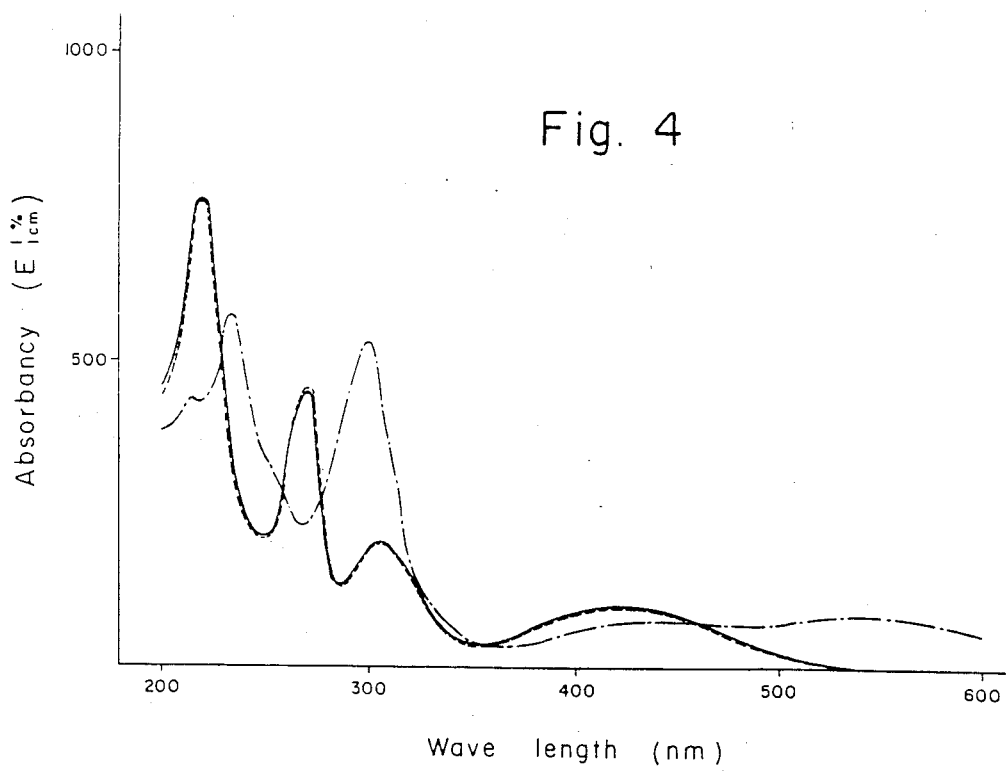

PHYSIOLOGICALLY ACTIVE SUBSTANCE P-23924, ITS PRODUCTION AND USE

The present invention relates to Physiologically Active Substance P-23924, its production and use.

Protocollagen prolyl hydroxylase is an enzyme which specifically hydroxylates the proline moiety of the protocollagen synthesized by ribosome in animal cells and is an important and rate-limiting factor in the biosynthesis of collagen. Among the compounds known to inhibit their enzyme activity are iron chelators (e.g. $\alpha,\alpha'$-dipyridyl etc.), SH enzyme inhibitors (e.g. p-chloromercury benzoate etc.) and certain heavy metals (e.g. $Cu^{++}$, $Zn^{++}$, etc.). However, because these substances invariably inhibit collagen biosynthesis nonspecifically, they cause serious side effects and cannot be used as drugs. If a substance was found that would not inhibit biosynthesis of non-collagenous proteins but would specifically inhibit collagen biosynthesis, such substance could be used for the prevention and treatment of organ fibrosis accompanied by an excessive accumulation of collagen such as arteriosclerosis, liver cirrhosis, scleroderma, keloid, rheumatic arthritis, pulmonary fibrosis, etc.

In their search for a substance capable of inhibiting protocollagen prolyl hydroxylase activity among microbial metabolites, the present inventors discovered that an actinomycete strain produces Physiologically Active Substance P-23924A, B, C, D, E and F which are novel inhibitors of collagen biosynthesis and that these compounds are convertible to their reduced forms. This finding was followed by further research which has resulted in the perfection of the present invention.

The present invention relates to (1) a compound represented by the formula:

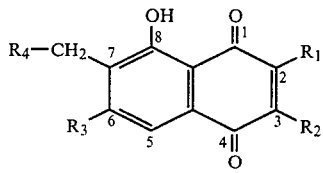

wherein $R_1$ is hydrogen, methyl or hydroxymethyl,
$R_2$ is hydrogen or methoxy,
$R_3$ is hydroxy or methoxy and
$R_4$ is hydrogen or a group

(2) a method of producing Physiologically Active Substance P-23924 A, B, C, D, E and/or F which comprises cultivating a microorganism belonging to the genus Streptomyces and capable of elaborating Physiologically Active Substance P-23924 A, B, C, D, E and/or F in a medium to cause said microorganism to elaborate and accumulate Physiologically Active Substance P-23924 A, B, C, D, E and/or F and recovering the same substance from the resulting culture broth, (3) a method of producing a compound represented by the formula

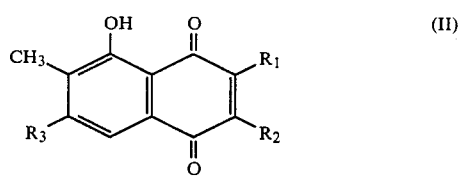

wherein $R_1$ is hydrogen, methyl or hydroxymethyl,
$R_2$ is hydrogen or methoxy, and
$R_3$ is hydroxy or methoxy,
which comprises subjecting to reduction a compound of the formula:

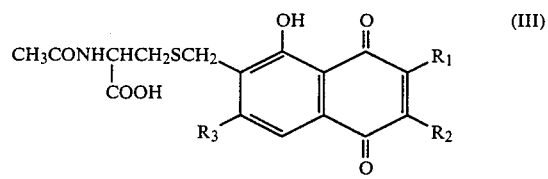

wherein $R_1$, $R_2$ and $R_3$ have the same meanings as defined above, and (4) an antifibriotic preparation containing Physiologically Active Substance P-23924.

The compounds of the compound (I) are named as follows:

| Name | Abbreviation | $R_1$ | $R_2$ | $R_3$ | $R_4$ |
|---|---|---|---|---|---|
| Physiologically Active Substance P-23924A | P-23924A | $-CH_3$ | $-H$ | $-OCH_3$ | $CH_3CONHCHCH_2S-$ <br> $\phantom{CH_3CONH}\vert$ <br> $\phantom{CH_3CON}COOH$ |
| Physiologically Active Substance P-23924B | P-23924B | $-CH_3$ | $-OCH_3$ | $-OCH_3$ | $CH_3CONHCHCH_2S-$ <br> $\phantom{CH_3CONH}\vert$ <br> $\phantom{CH_3CON}COOH$ |
| Physiologically Active Substance P-23924C | P-23924C | $-H$ | $-OCH_3$ | $-OCH_3$ | $CH_3CONHCHCH_2S-$ <br> $\phantom{CH_3CONH}\vert$ <br> $\phantom{CH_3CON}COOH$ |
| Physiologically Active Substance P-23924D | P-23924D | $-CH_3$ | $-OCH_3$ | $-OH$ | $CH_3CONHCHCH_2S-$ <br> $\phantom{CH_3CONH}\vert$ <br> $\phantom{CH_3CON}COOH$ |
| Physiologically Active Substance P-23924E | P-23924E | $-CH_2OH$ | $-H$ | $-OCH_3$ | $CH_3CONHCHCH_2S-$ <br> $\phantom{CH_3CONH}\vert$ <br> $\phantom{CH_3CON}COOH$ |

-continued

| Name | Abbreviation | R₁ | R₂ | R₃ | R₄ |
|---|---|---|---|---|---|
| Physiologically Active Substance P-23924F | P-23924F | —CH$_2$OH | —OCH$_3$ | —OCH$_3$ | CH$_3$CONHCHCH$_2$S—<br>\|<br>COOH |
| Physiologically Active Substance P-23924AR | P-23924AR | —CH$_3$ | —H | —OCH$_3$ | —H |
| Physiologically Active Substance P-23924BR | P-23924BR | —CH$_3$ | —OCH$_3$ | —OCH$_3$ | H |
| Physiologically Active Substance P-23924CR | P-23924CR | —H | —OCH$_3$ | —OCH$_3$ | H |
| Physiologically Active Substance P-23924DR | P-23924DR | —CH$_3$ | —OCH$_3$ | —OH | H |

Moreover, the compounds of the formula (I) will sometimes be referred to generically or individually as Physiologically Active Substances P-23924 or briefly as P-23924.

The microorganism employed in accordance with the present invention may be any strain of microorganism that belongs to the genus Streptomyces and is able to elaborate Physiologically Active Substance P-23924 A, B, C, D, E and/or F (which will sometimes be referred to briefly as a P-23924 producing strain).

As an example of the P-23924 producing strain, there may be mentioned Streptomyces sp. No. 23924 (hereinafter referred to briefly as Strain No. 23924) which was isolated from a soil sample collected in Ishigakijima, Okinawa Prefecture, Japan.

The characteristics of this Strain No. 23924 as determined in accordance with the methods described in International Journal of Systematic Bacteriology 16, No. 3, pp. 313-340 (1966) are as follows. Unless otherwise indicated, cultural characteristics were those found after 14 days incubation at 28° C.

(I) Morphology

Monopodially extending from vegetative mycelia are short sporulated filaments which are spiral or sometimes incompletely spiral, open-loop or hook-shaped, without whorl formation. Mature spore chains generally show 5 to 10 spores in chains. The spores are either cylindrical or elipsoidal and range in size from 0.4 to 0.7 by 0.7 to 1.2 microns, with smooth surfaces.

(II) Cultural characteristics

The degree of growth (G), growth and color of aerial mycelium (AM) and the production and color of soluble pigments (SP), among others, on various media are listed below. As to descriptions of colors, the standard color codes given in the Color Harmony Manual, Fourth Edition (1958) from Container Corporation of America were employed.

(a) Sucrose nitrate agar
  (G): Poor
  (AM): Sparse, light grayish brown (3 ge)
  (SP): None
(b) Glucose asparagine agar
  (G): Poor
  (AM): None
  (SP): None
(c) Glycerin asparagine agar
  (G): None
(d) Starch inorganic salt agar
  (G): Good -continued (AM): Abundant, powdery, gray (3 ih)
  (SP): Yellowish brown (4 gc)
(e) Tyrosine agar
  (G): Poor
  (AM): Sparse, gray (3 ba)
  (SP): Light yellowish red (4 ea)
(f) Nutrient agar
  (G): Moderate
  (AM): None
  (SP): None
(g) Yeast malt agar
  (G): Moderate
  (AM): Sparse, gray (3 fe)
  (SP): Light yellowish brown (4 ne)
(h) Oatmeal agar
  (G): Moderate
  (AM): Sparse, light grayish brown (3 ge)
  (SP): None
(III) Physiological characteristics
  (a) Temperature range for growth: 15-35° C.
  (b) Liquefaction of gelatin (glucose peptone gelatin, 24° C., 3 weeks): positive (weak)
  (c) Hydrolysis of starch: positive
  (d) Coagulation and peptonization of skim milk: both negative
  (e) Reduction of nitrate: negative
  (f) Production of melanoid pigment:
    Tyrosine agar: suspected positive
    Peptone yeast iron agar: negative
(IV) Assimilation of carbon sources (Pridham-Gottlieb agar)

| L-arabinose | ± | Inositol | — |
|---|---|---|---|
| D-xylose | ++ | L-rhamnose | — |
| D-glucose | ++ | Raffinose | — |
| D-fructose | ± | D-mannit | — |
| Sucrose | ± | Control | — |

(Note)
++: Good growth
±: Slight growth
—: No growth

It is apparent from the above descriptions of characteristics that this particular strain belongs to the genus Streptomyces.

The above Streptomyces sp. No. 23924 strain has been deposited at Institute for Fermentation, Osaka (IFO), Japan under the accession number of IFO 14205 since Sept. 20, 1982, and this microorganism, which was deposited on Oct. 1, 1982 at Fermentation Research Institute, Agency of Industrial Science and Technology, Ministry of International Trade and Industry (FRI), Japan under the accession number of FERM P-6739, the deposit being converted to a deposit under the Budapest Treaty, has been stored at FRI under the accession number of FERM BP-338.

Microorganisms of the genus Streptomyces are generally liable to change in characteristics and can be easily caused to undergo mutation by artificial procedures such as X-ray, ultraviolet ray or radioactive ray irradiation or by a treatment employing a mutagenic agent. Such mutants, only if they are able to produce P-23924 A, B, C, D, E and/or F, can all be employed for the purposes of the present invention.

The medium for cultivation of P-23924 producing strains may be a liquid medium or a solid medium and it is generally advantageous to conduct shake culture or aerobic submerged culture using a liquid medium. The medium may be of any kind only if it is suitable for growth of Actinomyces and for the production thereby of P-23924A, B, C, D, E and/or F. Thus, as sources of carbon, there may be employed glucose, lactose, glycerin, starch, sucrose, dextrin, molasses, organic acids (e.g. acetic acid, tartaric acid, etc.) and so on. As sources of nitrogen, there may be employed peptone, Casamino acid (Difco, U.S.A.), N-Z Amine A (Sheffield, U.S.A.) and other protein hydrolysates, yeast extract, malt extract, soybean meal, corn steep liquor, amino acids (e.g. aspartic acid, glutamic acid, etc.), various ammonium salts (e.g. ammonium sulfate, ammonium chloride, etc.) and so on. It is also possible to add inorganic salts such as various phosphates (e.g. sodium dihydrogen phosphate, potassium monohydrogen phosphate, etc.), metal salts (e.g. magnesium sulfate, sodium chloride, ferrous sulfate, etc.), heavy metal salts (e.g. manganese sulfate, zinc sulfate, etc.) and so on. For the purpose of promoting growth of the strain, vitamins (e.g. vitamin $B_1$, calcium pantothenate, etc.) nucleic acid related products (e.g. adenine, uracil, etc.), etc. may be added. Moreover, according to the cultural method and conditions used, the output of P-23924A, B, C, D, E and/or F may at times be increased by adding a defoaming agent such as silicone, polypropylene glycol ether derivative [e.g. Actocol (Takeda Chemical Industries, Ltd., Japan), etc.], soybean oil, etc. to the culture medium.

While the cultivation temperature and time, the pH of the medium, and other cultural conditions depend on the particular strain and the composition of the medium, they should be so selected and controlled that the output of P-23924 A, B, C, D, E and/or F will be maximal. It is in many cases desirable to conduct aerobic culture at about 20° to 40° C. for 24 to 240 hours while the pH of the medium is maintained at about 4 to 9. Recovery of Physiologically Active Substance P-23924 A, B, C, D, F and/or F from the culture broth can be easily accomplished by utilizing various procedures in a combination suited to the properties of the same substance. Among such procedures are extraction with an organic solvent which is neutral or weakly acidic and immiscible with water, such as ethyl acetate, butyl acetate, chloroform, butanol, benzene, toluene, diethyl ether, methylene chloride, methyl isobutyl ketone, etc., adsorption chromatography using activated carbon, silica gel, alumina, etc., gel filtration on a Sephadex column, ion exchange chromatography using ion exchange resins, and so on. By applying such procedures in a suitable combination, P-23924 A, B, C, D, E and/or F can be isolated as crystals or crystalline powders.

Various properties of Physiologically Active Substance P-23924 A, B, C, D, E and/or F as obtained in Example 2 which appears hereinafter are as follows.

(1) Physicochemical properties (a) Melting point: A 186° to 188° C.; B 200° to 202° C.; C 187° to 190° C.; D 205° to 207° C.; E 174° to 176° C.; F 191° to 195° C.

(b) Elemental analysis (Found):

| P-23924 | C | H | N | S |
|---|---|---|---|---|
| A | 54.75 ± 1.0 | 4.92 ± 0.5 | 3.77 ± 0.5 | 8.09 ± 0.5 |
| B | 53.74 ± 1.0 | 4.99 ± 0.5 | 3.26 ± 0.5 | 7.29 ± 0.5 |
| C | 52.43 ± 1.0 | 4.72 ± 0.5 | 3.50 ± 0.5 | 7.82 ± 0.5 |
| D | 52.58 ± 1.0 | 4.61 ± 0.5 | 3.55 ± 0.5 | 7.84 ± 0.5 |
| E | 52.18 ± 1.0 | 4.58 ± 0.5 | 3.19 ± 0.5 | 7.55 ± 0.5 |
| F | 51.67 ± 1.0 | 4.75 ± 0.5 | 3.45 ± 0.5 | 7.30 ± 0.5 |

(c) Molecular weight (based on mass spectrum) and molecular formula:

| P-23924 | Mol. wt. | Mol. formula |
|---|---|---|
| A | 393 | $C_{18}H_{19}NO_7S$ |
| B | 423 | $C_{19}H_{21}NO_8S$ |
| C | 409 | $C_{18}H_{19}NO_8S$ |
| D | 409 | $C_{18}H_{19}NO_8S$ |
| E | 409 | $C_{18}H_{19}NO_8S$ |
| F | 439 | $C_{19}H_{21}NO_9S$ |

(d) Specific rotation:

| P-23924 | $[\alpha]_D^{23}$ (in methanol) | C (%) |
|---|---|---|
| A | −91 ± 10° | 0.50 |
| B | −90 ± 10° | 0.51 |
| C | −93 ± 10° | 0.51 |
| D | −62 ± 10° | 0.51 |
| E | −86 ± 10° | 0.50 |
| F | −91 ± 10° | 0.51 |

(e) Solubility:

P-23924A, B, D and F are easily soluble in dimethyl sulfoxide, dimethylformamide, pyridine and 5% aqueous sodium hydrogen carbonate; soluble in methanol, dioxane and acetic acid; slightly soluble or insoluble in water, acetone, chloroform, n-hexane and petroleum ether. P-23924C is easily soluble in dimethyl sulfoxide, dimethylformamide, pyridine and 5% aqueous sodium hydrogen carbonate, soluble in methanol, dioxane, acetone and acetic acid; and slightly soluble or insoluble in water, chloroform, n-hexane and petroleum ether.

P-23924E is easily soluble in dimethyl sulfoxide, dimethylformamide, pyridine, 5% aqueous sodium hydrogen carbonate and methanol, soluble in dioxane and acetic acid, and slightly soluble or insoluble in water, chloroform; n-hexane and petroleum ether.

(f) Ultraviolet and visible absorption spectra:

See FIGS. 1 through 6. The wavelengths (nm) and $E_{1\ cm}^{1\%}$ values giving absorption peaks immediately after dissolution in the respective solvents are presented in Table 1. In FIGS. 1 through 6,——represents the values measured in methanol,——the values in 0.1N HCl-90% aqueous methanol,———the values measured in 0.1N NaOH-90% aqueous methanol.

TABLE 1

| | P-23924 | |
|---|---|---|
| A | B | C |

TABLE 1-continued

| Solvent | Wave length | ($E_{1cm}^{1\%}$) | Wave length | ($E_{1cm}^{1\%}$) | Wave length | ($E_{1cm}^{1\%}$) |
|---|---|---|---|---|---|---|
| Methanol | 220 ± 2 | (886 ± 90) | 220 ± 2 | (793 ± 80) | 221 ± 2 | (877 ± 90) |
| | 263 ± 2(sh) | (421 ± 45) | 262 ± 2 (sh) | (392 ± 40) | 260 ± 2(sh) | (398 ± 40) |
| | 270 ± 2 | (458 ± 50) | 268 ± 2 | (428 ± 40) | 265 ± 2 | (415 ± 40) |
| | 420 ± 10 | (129 ± 10) | 308 ± 2 | (214 ± 20) | 306 ± 2 | (256 ± 25) |
| | | | 420 ± 10 | | 420 ± 10 | (108 ± 10) | (124 ± 10) |
| 0.1N HCl | 221 ± 2 | (914 ± 90) | 220 ± 2 | (789 ± 80) | 221 ± 2 | (866 ± 90) |
| —90% aq. | 264 ± 2(sh) | (442 ± 45) | 261 ± 2(sh) | (390 ± 40) | 260 ± 2(sh) | (403 ± 40) |
| methanol | 270 ± 2 | (476 ± 50) | 268 ± 2 | (431 ± 45) | 266 ± 2 | (414 ± 40) |
| | 420 ± 10 | (133 ± 15) | 308 ± 2 | (210 ± 20) | 306 ± 2 | (250 ± 25) |
| | | | 420 ± 10 | (107 ± 10) | 420 ± 10 | (119 ± 10) |
| 0.1N NaOH | 216 ± 2 | (505 ± 50) | 216 ± 2 | (482 ± 50) | 216 ± 2 | (500 ± 50) |
| —90% aq. | 238 ± 2 | (681 ± 70) | 237 ± 2 | (748 ± 75) | 236 ± 2 | (791 ± 80) |
| methanol | 277 ± 2 | (248 ± 25) | 284 ± 2 | (215 ± 20) | 286 ± 2 | (213 ± 20) |
| | 540 ± 10 | (131 ± 15) | 540 ± 10 | (128 ± 15) | 540 ± 10 | (142 ± 15) |
| | See FIG. 1 | | See FIG. 2 | | See FIG. 3 | |

P-23924

| | D | | E | | F | |
|---|---|---|---|---|---|---|
| Solvent | Wave length | ($E_{1cm}^{1\%}$) | Wave length | ($E_{1cm}^{1\%}$) | Wave length | ($E_{1cm}^{1\%}$) |
| Methanol | 220 ± 2 | (764 ± 80) | 221 ± 2 | (851 ± 90) | 222 ± 2 | (866 ± 90) |
| | 271 ± 2 | (450 ± 45) | 263 ± 2(sh) | (393 ± 40) | 262 ± 2(sh) | (379 ± 40) |
| | 306 ± 2 | (209 ± 20) | 271 ± 2 | (435 ± 45) | 268 ± 2 | (381 ± 40) |
| | 420 ± 10 | (102 ± 10) | 420 ± 10 | (128 ± 10) | 308 ± 2 | (205 ± 20) |
| | | | | | 420 ± 15 | (91 ± 10) |
| 0.1N HCl | 220 ± 2 | (762 ± 80) | 221 ± 2 | (869 ± 90) | 221 ± 2 | (852 ± 90) |
| —90% aq. | 271 ± 2 | (456 ± 45) | 264 ± 2(sh) | (411 ± 40) | 262 ± 2(sh) | (374 ± 40) |
| methanol | 306 ± 2 | (207 ± 20) | 271 ± 2 | (445 ± 50) | 267 ± 2 | (383 ± 40) |
| | 420 ± 10 | (99 ± 10) | 420 ± 10 | (127 ± 15) | 307 ± 2 | (200 ± 20) |
| | | | | | 415 ± 15 | (107 ± 10) |
| 0.1N NaOH | 216 ± 2 | (438 ± 45) | 216 ± 2 | (478 ± 50) | 222 ± 2(sh) | (548 ± 60) |
| —90% aq. | 234 ± 2 | (576 ± 60) | 238 ± 2 | (633 ± 65) | 236 ± 2 | (730 ± 70) |
| methanol | 299 ± 2 | (531 ± 55) | 287 ± 2 | (231 ± 25) | 270 ± 2 | (257 ± 30) |
| | 540 ± 20 | (89 ± 10) | 540 ± 10 | (122 ± 15) | 542 ± 20 | (115 ± 10) |
| | See FIG. 4 | | See FIG. 5 | | See FIG. 6 | |

Sh = shoulder (g) Infrared absorption spectra:

The IR spectra by the potassium bromide disk method are shown in FIGS. 7 through 12. The main wave numbers giving absorption maxima are as follows.

(i) P-23924A
3300, 2930, 1710, 1665, 1640,
1620, 1570, 1540, 1500, 1460,
1420, 1380, 1335, 1280, 1240,
1200, 1180, 1110, 1040, 1000,
970, 900, 860, 800
See FIG. 7.

(ii) P-23924B
3300, 2950, 1725, 1705, 1660,
1630, 1590, 1540, 1460, 1420,
1370, 1330, 1300, 1270, 1210,
1190, 1170, 1130, 1100, 1060,
1020, 980, 950, 890, 860,
790, 760, 700
See FIG. 8.

(iii) P-23924C
3400, 3070, 2940, 1720, 1680,
1635, 1600, 1540, 1490, 1460,
1420, 1380, 1350, 1310, 1250,
1220, 1180, 1120, 1100, 1040,
990, 930, 880, 820, 800,
705
See FIG. 9.

(iv) P-23924D
3400, 3300, 2960, 1720, 1670,
1635, 1610, 1540, 1440, 1380,
1340, 1300, 1260, 1220, 1205,
1130, 1100, 1060, 1000, 900,
870, 820, 800, 780, 690
See FIG. 10.

(v) P-23924E
3550, 3300, 3080, 2950, 1725,
1660, 1640, 1610, 1570, 1540,
1490, 1455, 1420, 1380, 1325,
1300, 1240, 1210, 1180, 1120,
1080, 1040, 1010, 940, 920,
860, 820, 800, 770, 700
See FIG. 11.

(vi) P-23924F
3300, 1720, 1680, 1660, 1630,
1600, 1530, 1490, 1460, 1420,
1380, 1335, 1310, 1260, 1220,
1190, 1130, 1100, 1030, 1000,
980, 955, 870, 700
See FIG. 12.

(h) Color reactions:

All species of P-23924 A, B, C, D, E and F give positive ferric chloride, Rydon-Smith, alcoholic magnesium acetate reactions, and negative ninhydrin and Ehrlich reactions.

(i) Description:

All species of P-23924 A, B, C, D, E and F are acidic and fat-soluble substances occurring as crystals, crystalline powders or powders which are yellow to yellow-orange or orange-yellow in color.

(j) Nuclear magnetic resonance spectra:

The NMR spectra determined in dimethyl-$d_6$ sulfoxide at 400 MHz are shown in FIGS. 13 through 18. Characteristic signals are given below.

(i) P-23924A

δ DMSO-$d_6$ ppm: 1.86(3H, s), 2.09(3H, d, J=1.6 Hz), 2.71(1H, dd, J=8.8, 13.6 Hz), 2.91(1H, dd, J=5.0, 13.6 Hz), 3.66(1H, d, J=12.9 Hz), 3.78(1H, d, J=12.9 Hz), 3.96(3H, s), 4.47(1H, dt like, J=5.0, 8.3, 8.8 Hz), 6.89(1H, q, J=1.6 Hz), 7.09(1H, s), 8.18(1H, d, J=8.3 Hz), 12.40(1H, s) See FIG. 13.

(ii) P-23924B

δ DMSO-$d_6$ ppm: 1.86(3H, s), 1.95(3H, s), 2.70(1H, dd, J=8.8, 13.7 Hz), 2.89(1H, dd, J=4.9, 13.7 Hz), 3.65(1H, d, J=13.1 Hz), 3.77(1H, d, J=13.1 Hz), 3.95(3H, s), 4.03(3H, s), 4.47(1H, dt like, J=4.9, 8.1, 8.8 Hz), 7.11(1H, s), 8.18(1H, d, J=8.1 Hz), 12.59(1H, s) See FIG. 14.

(iii) P-23924C

δ DMSO-d<sub>6</sub> ppm: 1.85(3H, s), 2.71(1H, dd, J=8.8, 13.7 Hz), 2.91(1H, dd, J=4.9, 13.7 Hz), 3.66 (1H, d, J=12.9 Hz), 3.77(1H, d, J=12.9 Hz), 3.88 (3H, s), 3.95(3H, s), 4.47(1H, dt like, J=4.9, 8.1, 8.8 Hz), 6.26(1H, s), 7.15(1H, s), 8.18(1H, d, J=8.1 Hz), 12.73(1H, s) See FIG. 15.

(iv) P-23924D

δ DMSO-d<sub>6</sub> ppm: 1.85(3H, s), 1.94(3H, s), 2.73(1H, dd, J=8.8, 13.5 Hz), 2.92(1H, dd, J=4.8, 13.5 Hz), 3.64(1H, d, J=12.8 Hz), 3.76(1H, d, J=12.8 Hz), 4.00(3H, s), 4.48(1H, dt like, J=4.8, 8.1, 8.8 Hz), 7.03(1H, s), 8.17(1H, d, J=8.1 Hz), 12.79 (1H, s) See FIG. 16.

(v) P-23924E

δ DMSO-d<sub>6</sub> ppm: 1.85(3H, s), 2.71(1H, dd, J=8.5, 13.7 Hz), 2.90(1H, dd, J=4.9, 13.7 Hz), 3.67 (1H, d, J=13.1 Hz), 3.79(1H, d, J=13.1 Hz), 3.98 (3H, s), 4.47(2H, d, J=2.2 Hz), 4.47(1H, dt like, J=4.9, 8.1, 8.5 Hz), 5.47(1H, s), 6.82(1H, t, J=2.2 Hz), 7.15(1H, s), 8.18(1H, d, J=8.1 Hz), 12.29 (1H, s) See FIG. 17

(vi) P-23924F

δ DMSO-d<sub>6</sub> ppm: 1.85(3H, s), 2.70(1H, dd, J=8.8, 13.7 Hz), 2.9(1H, dd, J=4.9, 13.7 Hz), 3.67(1H, H, d, J=13.1Hz), 3.80(1H, d, J=13.1 Hz), 3.97(3H, s), 4.10 (3H, s), 4.36(2H, d, J=3.7 Hz), 4.47(1H, dt like, J=4.9, 8.3, 8.8 Hz), 4.93(1H, br t), 7.16(1H, s), 8.20(1H, d, J=8.3 Hz), 12.70(1H, s) See FIG. 18.

(k) Rf values on thin layer chromatograms:

The Rf values on silica gel plates (Merck, Article No. 5729, West Germany) and reverse-phase HPTLC plates (RP-8, Merck, Article No. 13725, West Germany) are as follows.

| Solvent | P-23924 | | | | | |
| --- | --- | --- | --- | --- | --- | --- |
| | A | B | C | D | E | F |
| (1) Silica gel plate, chloroform-acetic acid (8:2) | 0.39 | 0.42 | 0.30 | 0.19 | 0.12 | 0.22 |
| i-Propanol-acetic acid (96:4) | 0.45 | 0.48 | 0.29 | 0.57 | 0.45 | 0.39 |
| (2) Reverse-phase plate, methanol-water (7:3) | 0.61 | 0.55 | 0.69 | 0.60 | 0.75 | 0.72 |

Since there is not known any other compound having the above properties, P-23924 A, B, C, D, E and F are considered to be a novel substances.

Based on the above physicochemical properties, the following structural formula is proposed for P-23924 A, B, C, D, E and F.

| Compound | R<sub>1</sub> | R<sub>2</sub> | R<sub>3</sub> |
| --- | --- | --- | --- |
| P-23924A | CH<sub>3</sub> | H | OCH<sub>3</sub> |
| P-23924B | CH<sub>3</sub> | OCH<sub>3</sub> | OCH<sub>3</sub> |
| P-23924C | H | OCH<sub>3</sub> | OCH<sub>3</sub> |

-continued

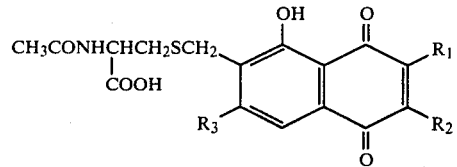

| Compound | R<sub>1</sub> | R<sub>2</sub> | R<sub>3</sub> |
| --- | --- | --- | --- |
| P-23924D | CH<sub>3</sub> | OCH<sub>3</sub> | OH |
| P-23924E | CH<sub>2</sub>OH | H | OCH<sub>3</sub> |
| P-23924F | CH<sub>2</sub>OH | OCH<sub>3</sub> | OCH<sub>3</sub> |

Having a free carboxyl group, compound (II) is capable of forming salts. The conventional method can be used for producing such salts. The salts include, for example, salts with calcium, magnesium, barium, sodium, potassium, manganese, iron, copper, zinc, etc.

The compound of the formula (I) wherein R<sub>4</sub> is hydrogen [compound (II)] is produced by means of reduction of the compound of the formula (I) wherein R<sub>4</sub> is a group $$CH_3CONHCHCH_2S-$$
$$|$$
$$COOH$$

[compound (III)].

The reduction is conducted by the manner per se known, such as catalytic reduction, electrolytic reduction and reduction using a reducing agent.

When the reduction is practiced by catalytic reduction, i.e. by reduction in the presence of a catalyst, the following procedure may be followed. Thus, the compound (III) is first dissolved in a routine solvent [e.g. alcohol (e.g. methanol, ethanol, isopropanol, etc.), dioxane, tetrahydrofuran, dimethylformamide or a mixture of such solvents] and hydrogen gas is bubbled into the solution in the presence of a catalyst [e.g. Raney nickel, palladium on carbon, palladium barium carbonate, platinum oxide, rhodium complex, Raney type catalyst of cobalt, Raney type catalyst of iron, Raney type catalyst of copper]. This reaction is carried out at a temperature of 20° to 100° C., desirably at 60° to 80° C. for 10 minutes to 10 hours. While the reaction proceeds readily at atmospheric pressure, one may conduct it at elevated pressures between 5 to 200 kg/cm<sup>2</sup>.

When the reduction is to be practiced employing a reducing agent, the compound (III) is treated with a reducing agent [for example, a metal hydride (e.g. lithium aluminum hydride, sodium borohydride, tributyltin hydride, etc.), alkali metal (e.g. lithium, sodium, etc.), a metal salt (e.g. divalent chromium salts such as chromous chloride, chromous acetate, etc.) or zinc or amalgamated zinc] in a suitable solvent [e.g. methanol, ethanol, t-butanol, amylalcohol, dimethylformamide, dioxane, tetrahydrofuran, dimethylsulfoxide, ethylene glycol, ethylenediamine, diethylenetriamine, etc.]. The method is practiced at a temperature of from −50° C. to 150° C. and, for better results, at room temperature to 80° C. for 0.5 to 10 hours.

When electrolytic reduction is used, the starting compound is dissolved in a suitable solvent and, then, the routine procedure is applied. For example, the compound (III) is dissolved in a solvent [e.g. alcohol (e.g. methanol, ethanol, etc.), ammonia, dimethylformamide, etc.] and the reduction is carried out using a low overvoltage electrode (e.g. platinum, wolfram, etc.) or a high overvoltage electrode (e.g. lead, zinc, mercury, etc.). Better results are sometimes obtained when the pH of the solution is brought to acidic, for example to pH 3 to 5.

The reaction is carried out for one hour to 5 hours, at a temperature between about 20° and 100° C. preferably between about 60° and 80° C.

The recovery of thus produced compound (II) can be carried out by the manner described as above.

The following is the physico-chemical properties of P-23924 AR, BR, CR and DR obtained in the Examples 3 to 6. In the following, P-23924 AR is referred to briefly as AR, P-23924 BR as BR, P-23924 CR as CR and P-23924 DR as DR.

(a) Melting point: AR 145° to 149° C.; BR 156° to 159° C.; CR 210° to 212° C.; DR 263° to 266° C.

(b) Elemental analysis (Found):

|  | C | H |
|---|---|---|
| AR | 66.99 ± 1.0 | 5.27 ± 0.5 |
| BR | 63.93 ± 1.0 | 5.52 ± 0.5 |
| CR | 62.96 ± 1.0 | 5.10 ± 0.5 |
| DR | 63.03 ± 1.0 | 4.99 ± 0.5 |

(c) Molecular weight (based on mass spectrum) and molecular formula:

|  | Mol. wt. | Mol. formula |
|---|---|---|
| AR | 232 | $C_{13}H_{12}O_4$ |
| BR | 262 | $C_{14}H_{14}O_5$ |
| CR | 248 | $C_{13}H_{12}O_5$ |
| DR | 248 | $C_{13}H_{12}O_5$ |

(d) Specific rotation:

|  | $[\alpha]_D^{23}$ in dimethylsulfoxide | C (%) |
|---|---|---|
| AR | 0 | 0.20 |
| BR | 0 | 0.20 |
| CR | 0 | 0.20 |
| DR | 0 | 0.20 |

(e) Solubility: AR, BR, CR and DR are readily or easily soluble in dimethylsulfoxide, pyridine, ethyl acetate, chloroform, dioxan; slightly soluble or insoluble in water, n-hexane, petroleum ether.

(f) Ultraviolet and visible absorption spectra:

See FIGS. 19 through 22. The wavelengths (nm) and $E_{1\ cm}^{1\%}$ values giving absorption peaks immediately after dissolution in the respective solvents are presented in Table 3. In FIGS. 19 through 22, —— represents the values measured in methanol, ----- the values in 0.1N HCl-90% aqueous methanol, --- the values measured in 0.1N NaOH-90% aqueous methanol.

TABLE 3

| Solvent | Wave length ($E_{1cm}^{1\%}$) | | | |
|---|---|---|---|---|
|  | AR | BR | CR | DR |
| Methanol | 219 ± 2 (1374 ± 140) | 218 ± 2 (1310 ± 130) | 218 ± 2 (1417 ± 140) | 218 ± 2 (1288 ± 130) |
|  | 260 ± 2* (688 ± 70) | 260 ± 2* (677 ± 70) | 256 ± 2* (708 ± 70) | 267 ± 2 (761 ± 80) |
|  | 265 ± 2 (705 ± 70) | 264 ± 2 (713 ± 70) | 262 ± 2 (739 ± 70) | 303 ± 2 (407 ± 40) |
|  | 283 ± 2* (314 ± 30) | 308 ± 2 (371 ± 40) | 305 ± 2 (441 ± 40) | 425 ± 10 (170 ± 20) |
|  | 420 ± 10 (183 ± 20) | 420 ± 10 (162 ± 20) | 425 ± 10 (188 ± 20) |  |
| 0.1N HCl —90% aqueous methanol | 219 ± 2 (1396 ± 140) | 218 ± 2 (1294 ± 130) | 218 ± 2 (1417 ± 140) | 218 ± 2 (1314 ± 130) |
|  | 260 ± 2* (709 ± 70) | 259 ± 2* (674 ± 70) | 256 ± 2* (736 ± 70) | 267 ± 2 (791 ± 80) |
|  | 266 ± 2 (728 ± 70) | 264 ± 2 (722 ± 70) | 263 ± 2 (771 ± 80) | 306 ± 2 (391 ± 40) |
|  | 283 ± 2* (333 ± 30) | 308 ± 2 (365 ± 40) | 307 ± 2 (448 ± 50) | 425 ± 10 (174 ± 20) |
|  | 420 ± 10 (188 ± 20) | 425 ± 10 (165 ± 20) | 425 ± 10 (195 ± 20) |  |
| 0.1N NaOH— 90% aqueous methanol | 234 ± 2 (1036 ± 100) | 234 ± 2 (1111 ± 110) | 233 ± 2 (1224 ± 120) | 230 ± 2 (1038 ± 100) |
|  | 259 ± 10 (447 ± 50) | 266 ± 2 (416 ± 40) | 260 ± 2 (409 ± 40) | 292 ± 2 (970 ± 100) |
|  | 283 ± 2* (391 ± 40) | 295 ± 15* (294 ± 60) | 285 ± 2 (343 ± 30) | 440 ± 20 (149 ± 15) |
|  | 425 ± 20 (99 ± 10) | 420 ± 20 (79 ± 10) | 305 ± 2* (329 ± 30) | 535 ± 20 (143 ± 20) |
|  | 535 ± 20 (181 ± 20) | 530 ± 20 (166 ± 20) | 535 ± 20 (203 ± 20) |  |
|  | See FIG. 19 | See FIG. 20 | See FIG. 21 | See FIG. 22 |

*Shoulder (g) Infrared absorption spectra:

The IR spectra by the potassium bromide disk method are shown in FIGS. 23 to 26. The main wave numbers giving absorption maxima are as follows.

(1) AR
3400–3450, 2900–3000, 1660, 1630, 1605, 1570, 1490, 1420, 1370, 1330, 1310, 1275, 1240, 1200, 1165, 1140, 1060, 1000, 910, 870, 810, 800, 700, 620 See FIG. 23.

(2) BR
3400–3500, 2960, 1670, 1630, 1600, 1490, 1455, 1420, 1380, 1330, 1290, 1230, 1220, 1150, 1110, 1080, 1020, 980, 920, 870, 820, 790, 705 See FIG. 24.

(3) CR
3400–3450, 2930, 1680, 1640, 1600, 1485, 1420, 1380, 1350, 1310, 1260, 1250, 1220, 1210, 1140, 1120, 1015, 980, 960, 920, 870, 850, 790, 710 See FIG. 25.

(4) DR
3430, 2950, 1655, 1620, 1595, 1490, 1450, 1430, 1360, 1310, 1290, 1220, 1130, 1100, 1080, 1020, 940, 890, 865, 830, 785, 760, 710, 685 See FIG. 26.

(h) Color reactions: AR, BR, CR and DR give positive ferric chloride, reduction with hydrosulfite; and negative ninhydrin and p-anisaldehyde-sulfuric acid reaction.

(i) Nuclear magnetic resonance spectra:

The NMR spectra determined in dimethyl-$d_6$ sulfoxide at 400 MHz are shown in FIGS. 27 to 30. Characteristic signals are given below.

(1) AR
δ DMSO-$d_6$ ppm: 2.085(3H,d,J=1.6 Hz,2-CH$_3$), 6.867 (1H,q,J=1.6 Hz,3-H), 7.057(1H,S,5-H), 3.952(3H,S,6-OCH$_3$), 2.049(3H,S,7-CH$_3$), 12.314(1H,S,disappeared on D$_2$O,8-OH) See FIG. 27

(2) BR
δ DMSO-$d_6$ ppm: 1.949(3H, S, 2-CH$_3$), 4.026(3H, S, 3-OCH$_3$), 7.100(1H, S, 5-H), 3.949(3H, S, 6-OCH$_3$), 2.053(3H, S, 7-CH$_3$), 12.510(1H, S, disappeared on D$_2$O, 8-OH) See FIG. 28

(3) CR

δ DMSO-$d_6$ ppm: 6.242(1H, S, 2-H), 3.870(3H, S, 3-OCH$_3$), 7.127(1H, S, 5-H), 3.949(3H, S, 6-OCH$_3$), 2.063(3H, S, 7-CH$_3$), 12.631 (1H, S, disappeared on D$_2$O, 8-OH). See FIG. 29

(4) DR

δ DMSO-$d_6$ ppm: 1.918(3H, S, 2 or 7-CH$_3$), 3.993(3H, S, 3-OCH$_3$), 6.989(1H, S, 5-H), 10.940(1H, S, disappeared on D$_2$O, 6-OH), 2.005(3H, S 2 or 7-CH$_3$), 12.637(1H, S, disappeared on D$_2$O, 8-OH) See FIG. 30

(k) Rf values on thin layer chromatograms:

The Rf values on silica gel plates (Merck, Article No. 5729, West Germany) and reverse-phase HPTLC plates (RP-18, Merck, Article No. 13724) are as follows.

| | Solvent | AR | BR | CR | DR |
|---|---|---|---|---|---|
| (1) | Silica gel plate, ethyl acetate-n-hexane (1:5) | 0.65 | 0.72 | 0.29 | 0.35 |
| | Chloroform | 0.82 | 0.83 | 0.50 | 0.15 |
| (2) | Reverse-phase plate, methanol | 0.54 | 0.50 | 0.61 | 0.69 |

Biological properties of P-23924 are as follows.

(a) Protocollagen prolyl hydroxylase inhibiting activity: This inhibitory activity was assayed by the method of R. E. Rhoads [Methods in Enzymology XVII B, 306 (1971)] using a partially purified enzyme preparation derived from chick embryo in accordance with the methods of K. I. Kivirriko et al and J. Halme et al. [Journal of Biological Chemistry 242, 4007 (1967) and Biochimica et Biophysica Acta 198, 460 (1967)] and, as the substrate, (Pro-Pro-Gly)$_5$.4H$_2$O [manufactured by Tanpakushitsu Kenkyu Shoreikai (Protein Research Foundation Society), Osaka, Japan]. The concentrations of P-23924 required for a 50% inhibition of 100 μg (as protein) of said partially purified enzyme preparation were as follows.

P-23924A: $6.7 \times 10^{-5}$M
P-23924B: $9.5 \times 10^{-5}$M
P-23924C: $5.7 \times 10^{-5}$M
P-23924D: $2.7 \times 10^{-4}$M
P-23924E: $2.1 \times 10^{-5}$M
P-23924F: $2.1 \times 10^{-5}$M On the other hand, by a similar procedure as above, the protocollagen prolyl hydroxylase inhibiting activities on the compounds of P-23924 AR, BR, CR and DR are measured.

The results are shown in the following table.

| Compound | Concentration of the compound (μM) | Amount of the enzyme used (μg) | Inhibition (%) |
|---|---|---|---|
| P-23924 AR | 12.5 | 100 | 26 |
| | 3.13 | 20 | 37 |
| P-23924 BR | 12.5 | 100 | 22 |
| | 3.13 | 20 | 26 |
| P-23924 CR | 12.5 | 100 | 33 |
| | 3.13 | 20 | 40 |
| P-23924 DR | 12.5 | 100 | 20 |
| | 3.13 | 20 | 33 |

The above results indicate that P-23924 has strong inhibitory activity against protocollagen prolyl hydroxylase activity.

(b) Collagen biosynthesis suppressant activity: In accordance with the method of T. Ishimaru et al [Biochemical Pharmacology 31, 915 (1982)], P-23924 was intraperitoneally administered to SD rats (females, 3 weeks old) once daily for 6 consecutive days and the collagen content and non-collagenous protein content of the uterus were compared with those of control animals. As shown in Table 4, P-23924 caused a selective and significant suppression of collagen biosynthesis.

TABLE 4

| Group | Body weight of rats (g) | Total protein content of uterus (mg) | Collagen content of uterus (mg) | % Inhibition* Collagen | Non-collagenous protein** |
|---|---|---|---|---|---|
| (A) Control (1) 5% ethanol-saline*** | 75 ± 4 | 8.93 ± 0.70 | 1.71 ± 0.09 | — | — |
| (B) Control (2) Estradiol-17β(5 μg) | 72 ± 5 | 16.74 ± 1.97 | 2.94 35 0.45 | — | — |
| (C) Treatment | | | | | |
| Estradiol-17β(5 μg) +P-23924A(1 mg/kg) | 73 ± 3 | 15.67 ± 1.63 | 2.53 ± 0.35 (P < 0.05) | 33 | 10 |
| Estradiol-17β(5 μg) +P-23924B(1 mg/kg) | 70 ± 5 | 14.92 ± 1.55 | 2.37 ± 0.43 (P < 0.02) | 46 | 19 |
| Estradiol-17β(5 μg) +P-23924C(1 mg/kg) | 73 ± 6 | 14.01 ± 1.51 | 2.19 ± 0.49 (P < 0.01) | 61 | 30 |
| Estradiol-17β(5 μg) +P-23924D(50 mg/kg) | 72 ± 3 | 15.63 ± 1.43 | 2.55 ± 0.30 (P< 0.05) | 32 | 11 |
| Estradiol-17β(5 μg) +P-23924E(1 mg/kg) | 72 ± 4 | 15.73 ± 1.59 | 2.52 ± 0.36 (P < 0.05) | 34 | 9 |
| Estradiol-17β(5 μg) +P-23924F(1 mg/kg) | 71 ± 3 | 15.20 ± 1.53 | 2.47 ± 0.57 (P < 0.05) | 38 | 15 |

The marginal notes of the portion asterisked in the Table 4 are shown in below.

*Degree of inhibition (%) = $\frac{(B) - (C)}{(B) - (A)} \times 100$

**Non-collagenous protein = total protein content − collagen content

***Estradiol-17β was dissolved in 5% ethanol/physiological saline. In said tests, rats were used in groups of 10 individuals.

The acute toxicity [LD$_{50}$] values of P-23924 in rats by the intraperitoneal route are given below.

P-23924A: 100 to 200 mg/kg,
P-23924B: 50 to 100 mg/kg,
P-23924C: 100 to 200 mg/kg,
P-23924D: more than 400 mg/kg,
P-23924E: Ca. 50 mg/kg,
P-23924F: 50 to 100 mg/kg.

Therefore, it is assumed that P-23924 is low toxicity.

As mentioned hereinbefore, P-23924 has protocollagen prolyl hydroxylase inhibiting and/or selective collagen biosynthesis suppressant activities and is low toxicity, and is therefore of use as inhibitors of animal tissue fibrosis, biochemical reagents, and so forth.

Thus, P-23924 is of use as a prophylactic/therapeutic agent against organ fibrosis in mammals (e.g. rabbit, rat, mouse, dog, cat, man, etc.) and can be administered to such animals for the prevention and treatment of pulmonary fibrosis, liver cirrhosis, nephrosclerosis, arteriosclerosis scleroderma, myelofibrosis, chronic arthritis, etc.

The dose of P-23924 varies with the disease, condition, subject, route of administration, etc. For the prevention/treatment of organ fibrosis, about 0.2 to 20 mg/kg preferably about 2 to 20 mg/kg per day per the mammal is administered in a single dose to 3 divided doses.

P-23924 can be orally or parenterally administered as such or in combination with a pharmaceutically acceptable carrier, excipient or diluent in such dosage forms as powders, granules, tablets, capsules, injections, etc.

In the production of oral preparations, there may be employed suitable amounts of binders (e.g. hydroxypropyl-cellulose, hydroxypropylmethyl-cellulose, macrogol, etc.), disintegrators (e.g. starch, carboxymethylcellulose calcium, etc.), excipients (e.g. lactose, starch, etc.), lubricants (e.g. magnesium stearate, talc, etc.) and so on.

In the production of parenteral or non-oral preparations, e.g. injections, there may be employed isotonicating agents (e.g. glucose, D-sorbitol, D-mannitol, sodium chloride, etc.), preservatives (e.g. benzyl alcohol, chlorobutanol, methyl p-hydroxybenzoate, propyl p-phydroxybenzoate, etc.), buffers (e.g. phosphate buffer, sodium acetate buffer, etc.) and so on.

P-23924 can also be used as biochemical reagents, for example as an inhibitor of collagen biosynthesis in cultured animal cells or as a specific inhibitor of protocollagen prolyl hydroxylase activity.

BRIEF DESCRIPTION OF THE DRAWINGS

FIGS. 1 to 6 and 19 to 22 show ultraviolet and visible absorption spectra of Physiologically Active Substances P-23924 A, B, C, D, E, F, AR, BR, CR and DR respectively.

Figure 1:
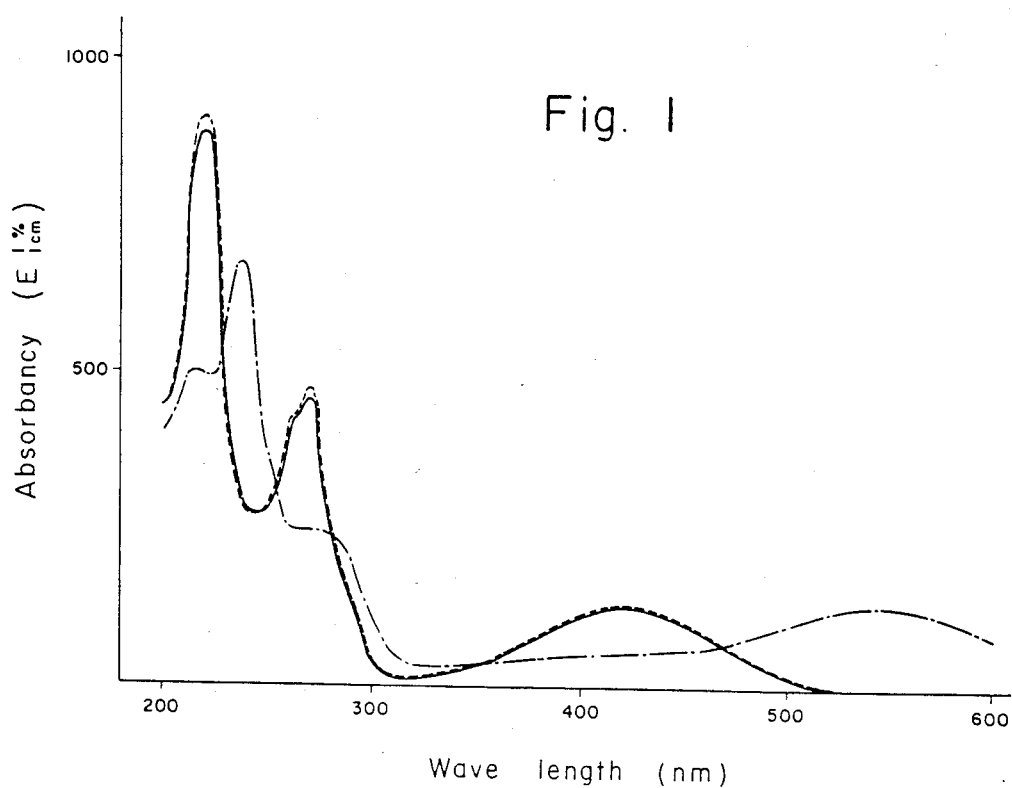
Figure 2:
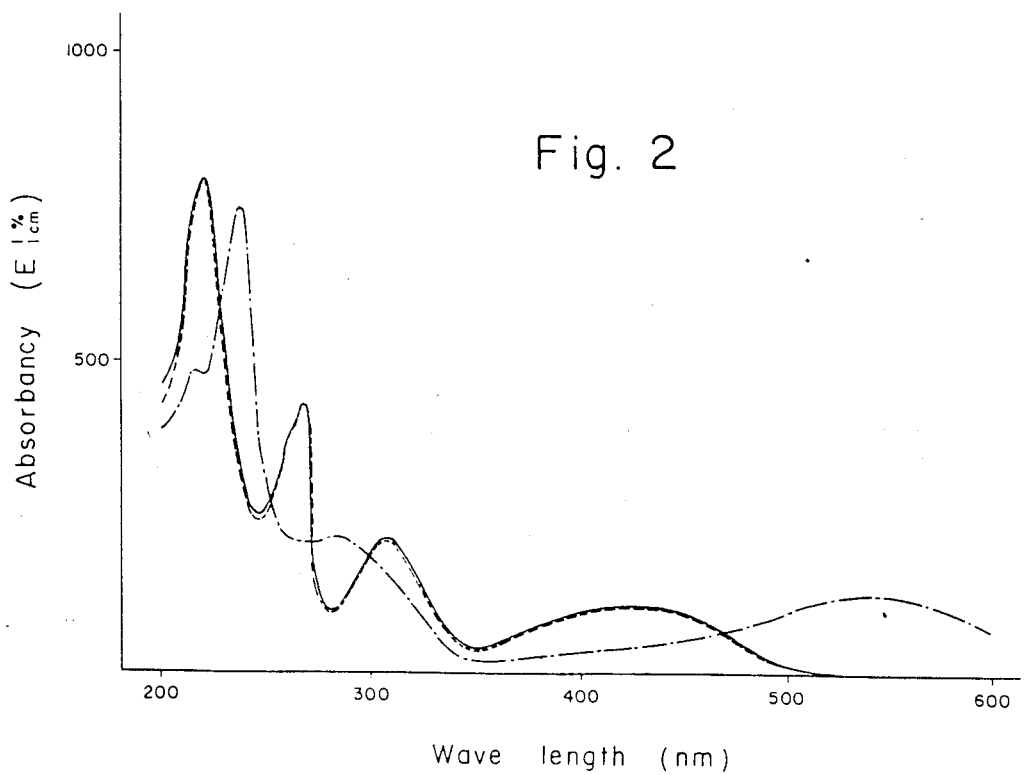
Figure 5:
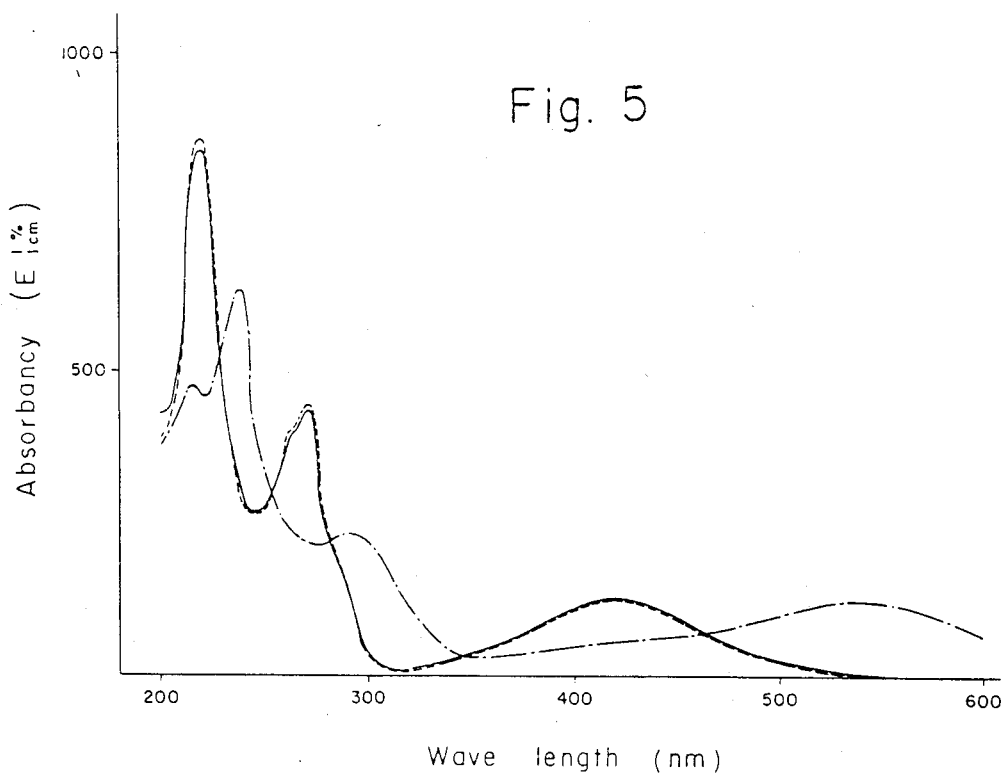
Figure 6:
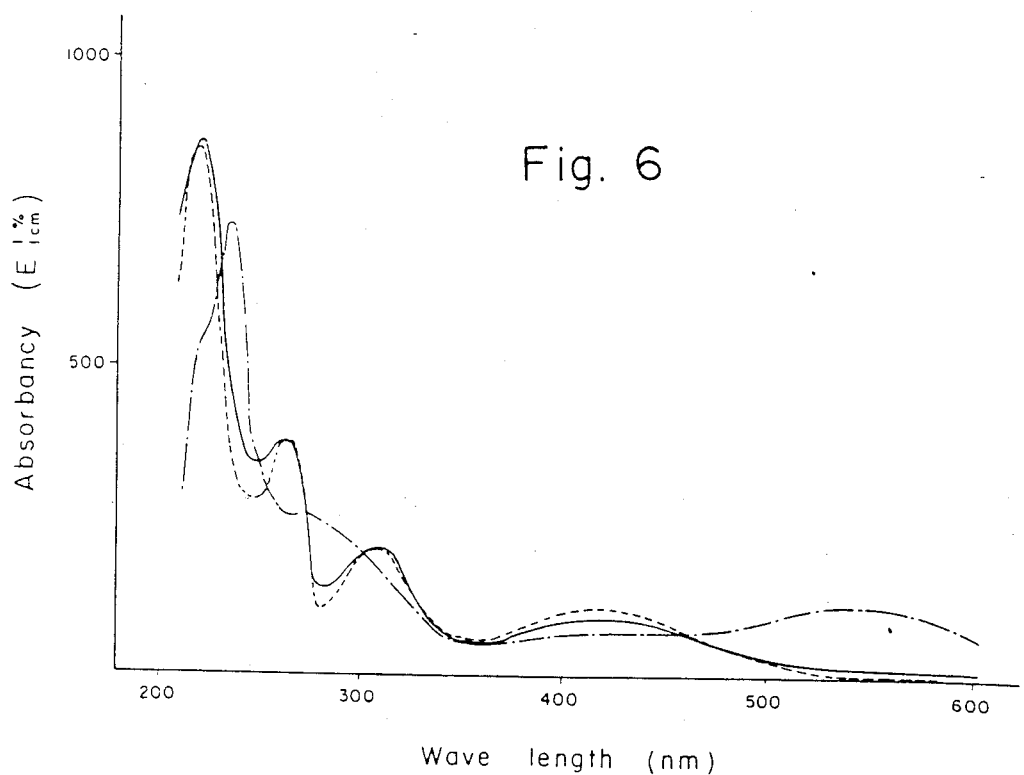
Figure 7:
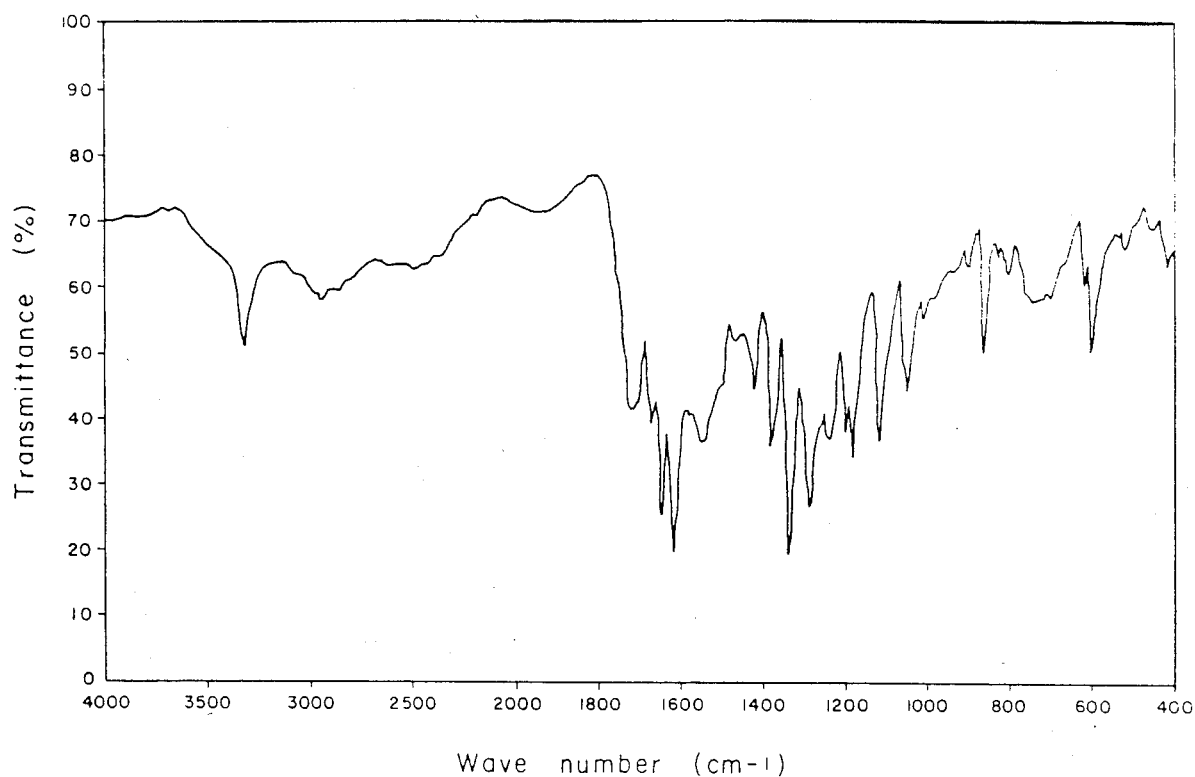
FIGS. 7 to 12 and 23 to 26, infrared absorption spectra of said substances, respectively.
Figure 8:
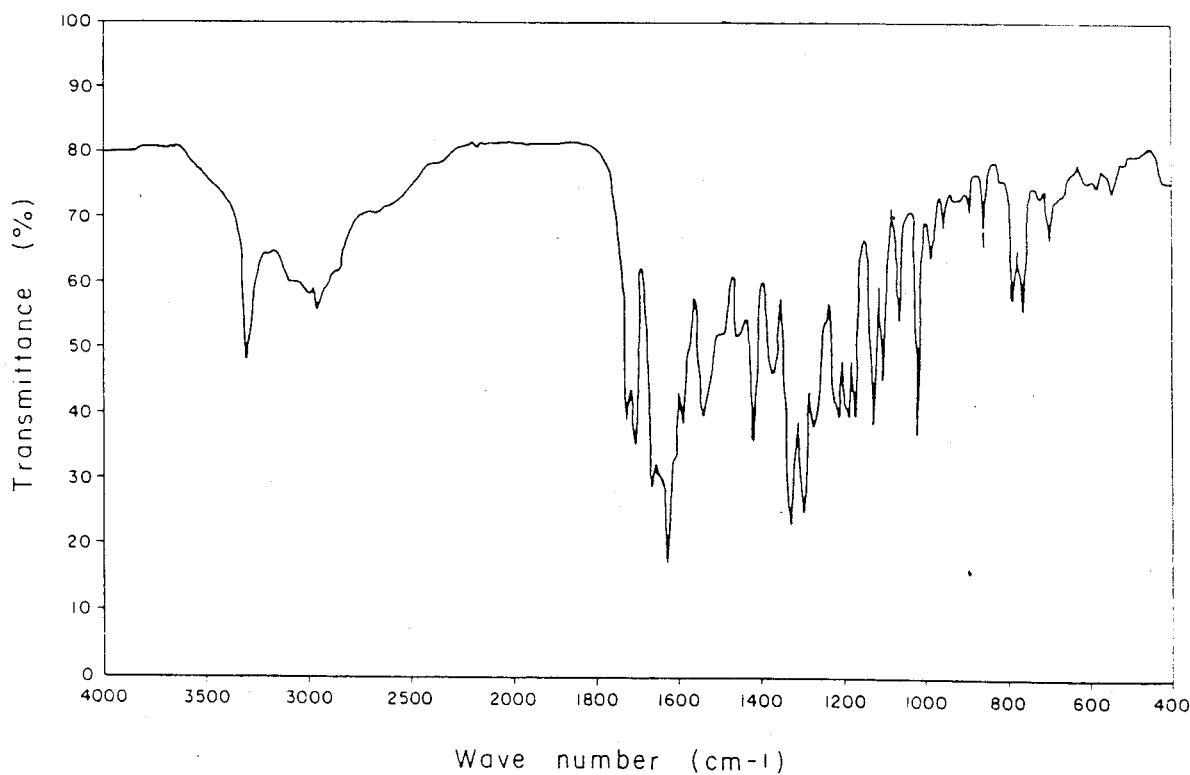
Figure 9:
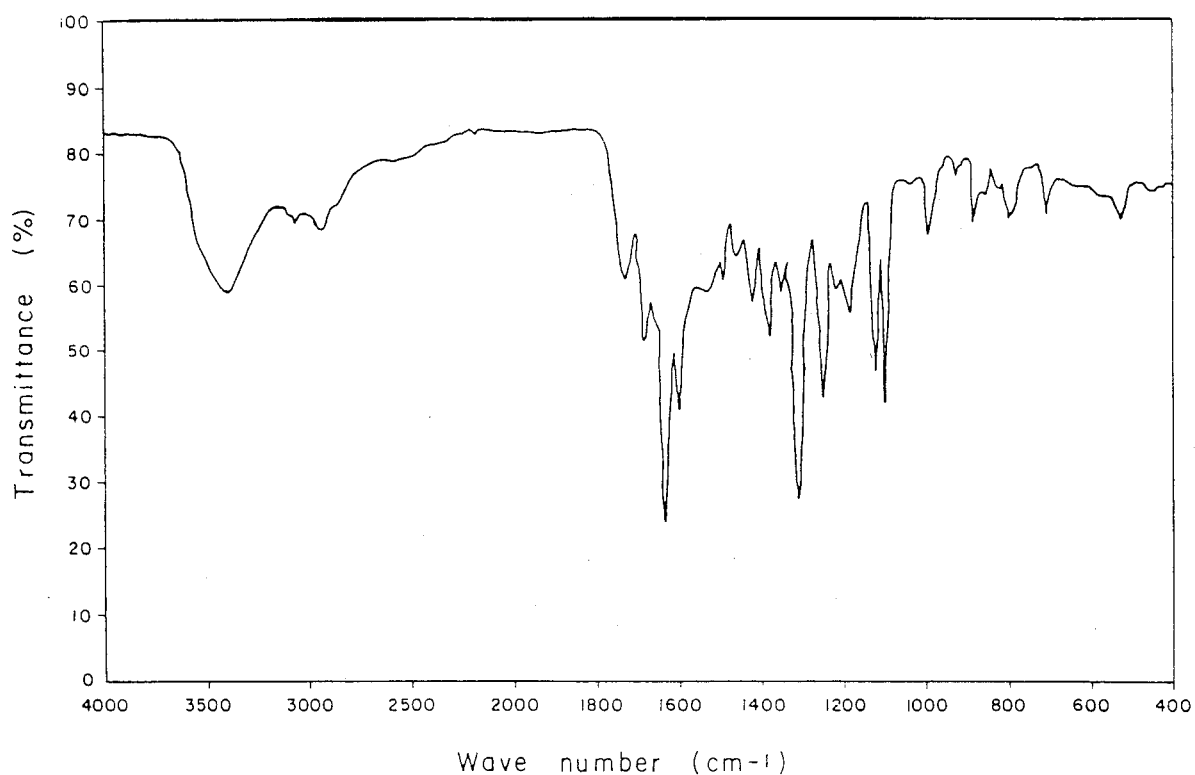
Figure 10:
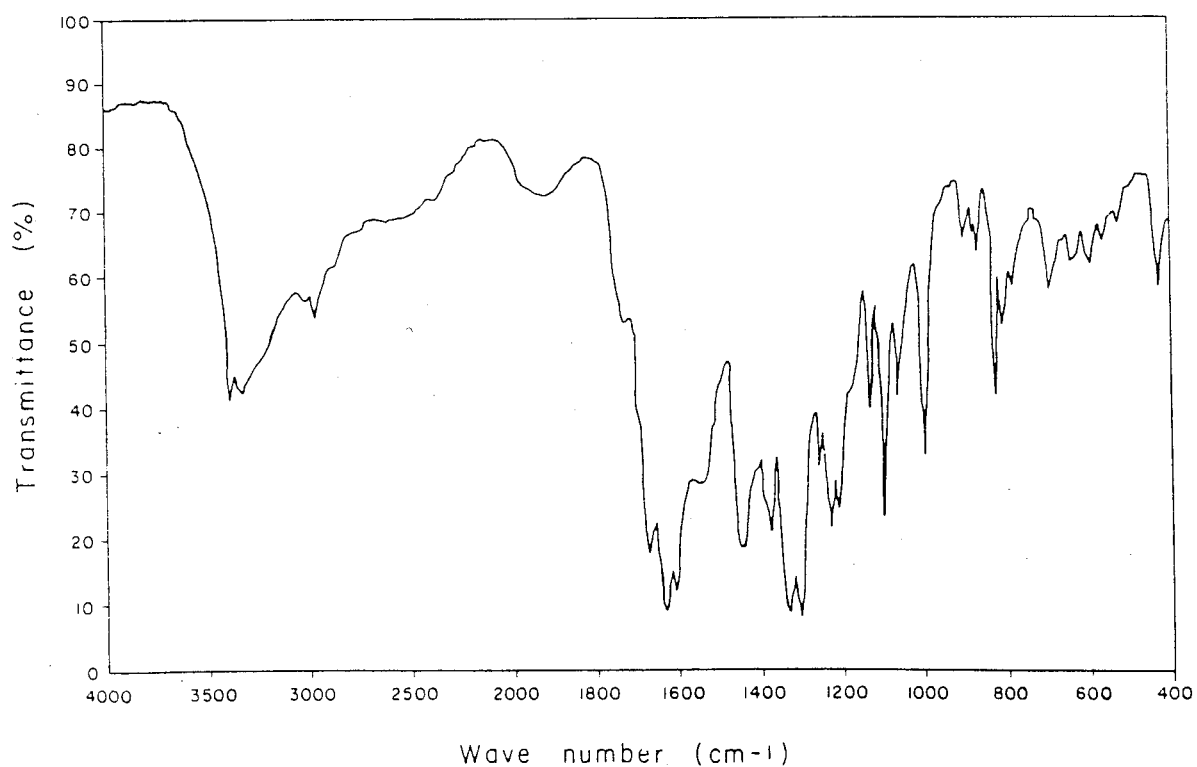
Figure 11:
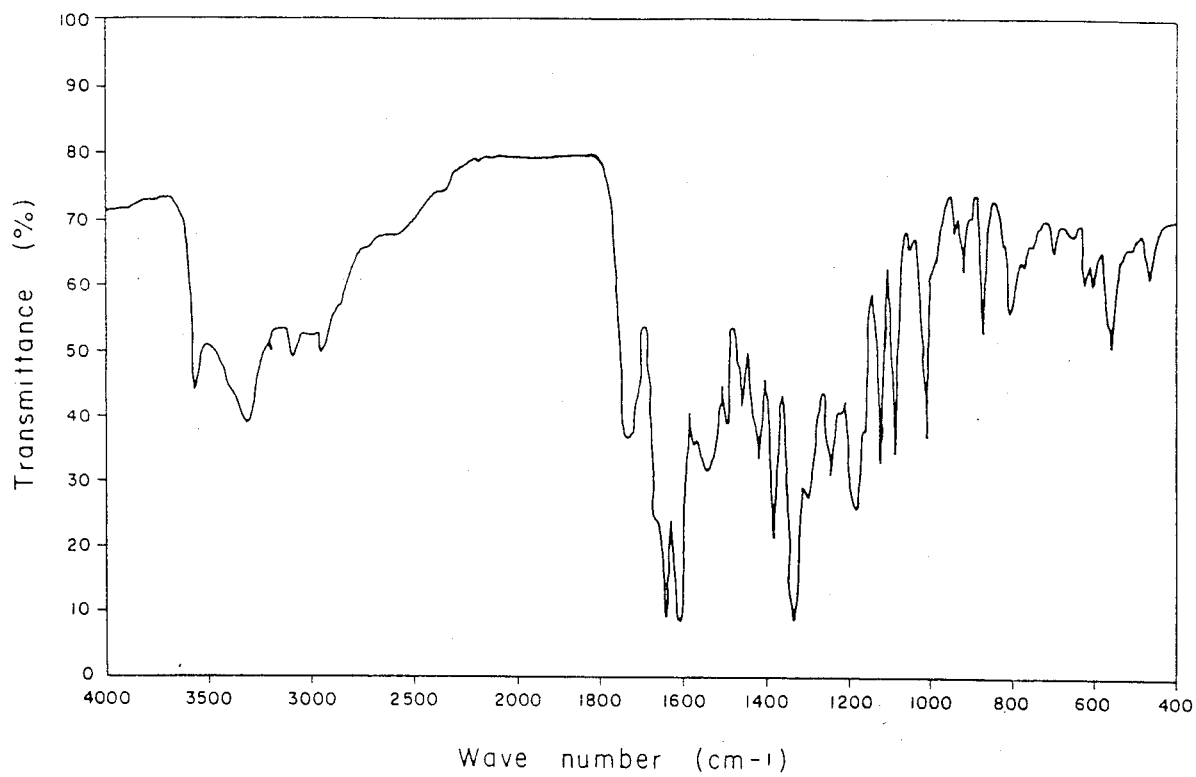
Figure 12:
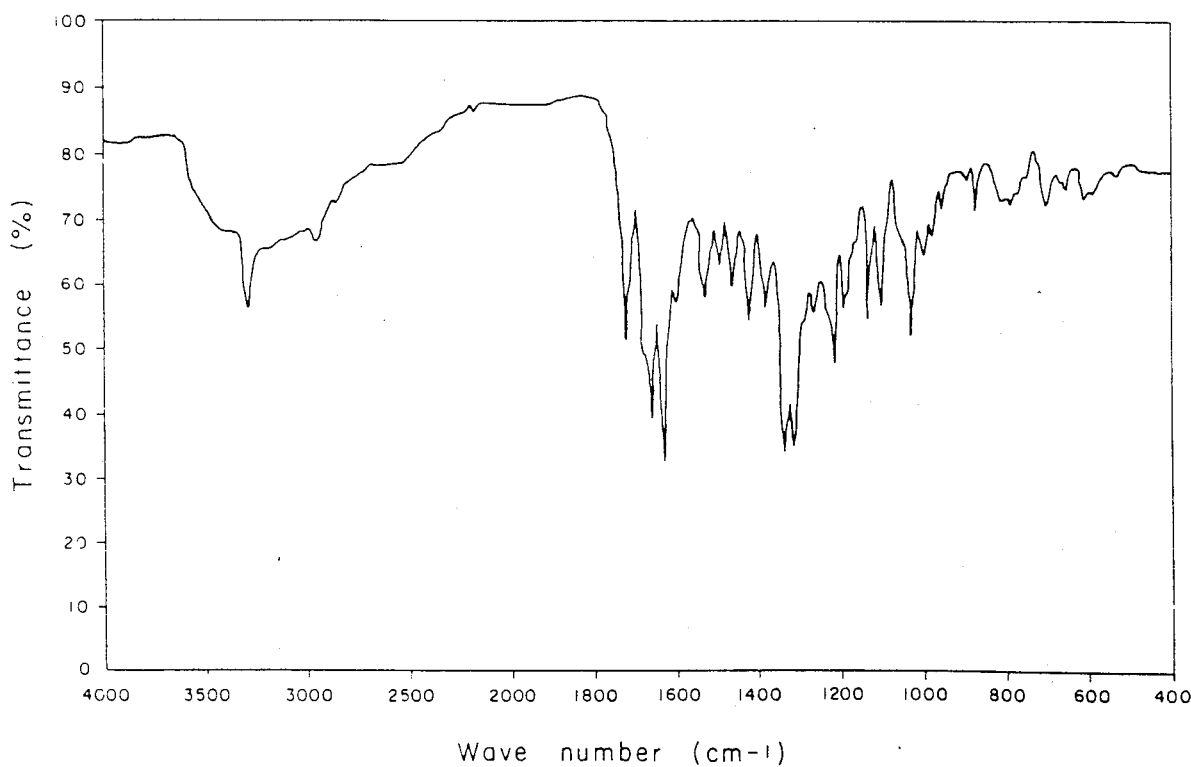
Figure 13:
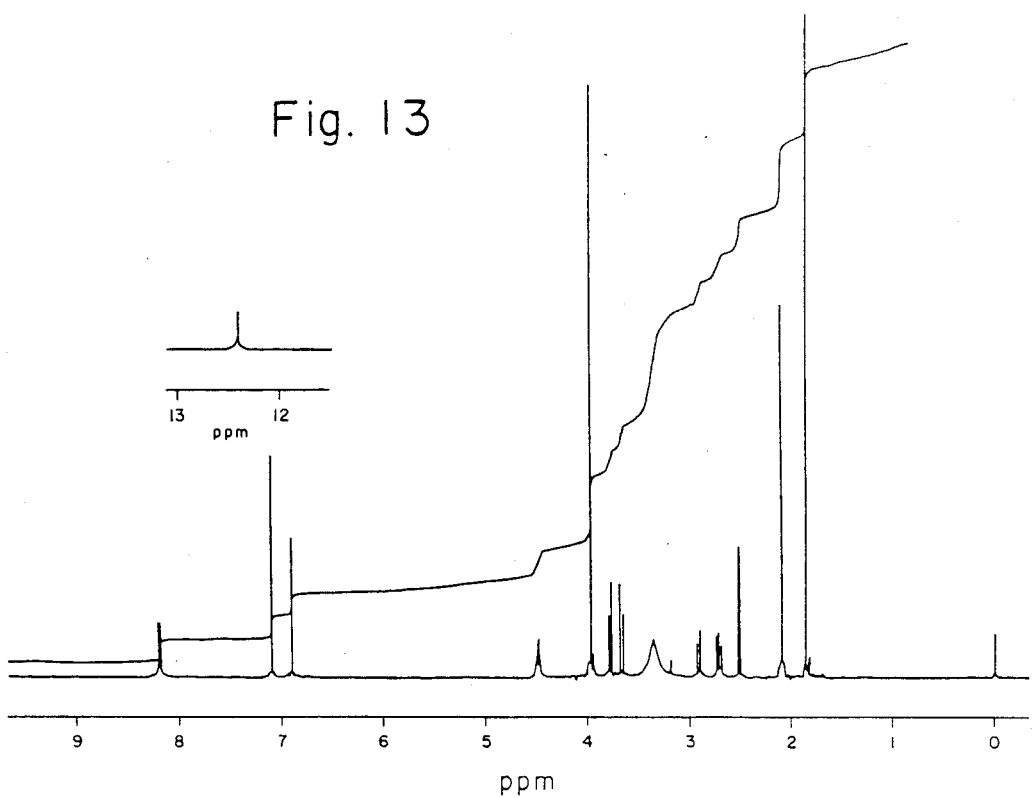
FIGS. 13 to 18 and 27 to 30, nuclear magnetic resonance spectra of said substances, respectively.
Figure 14:
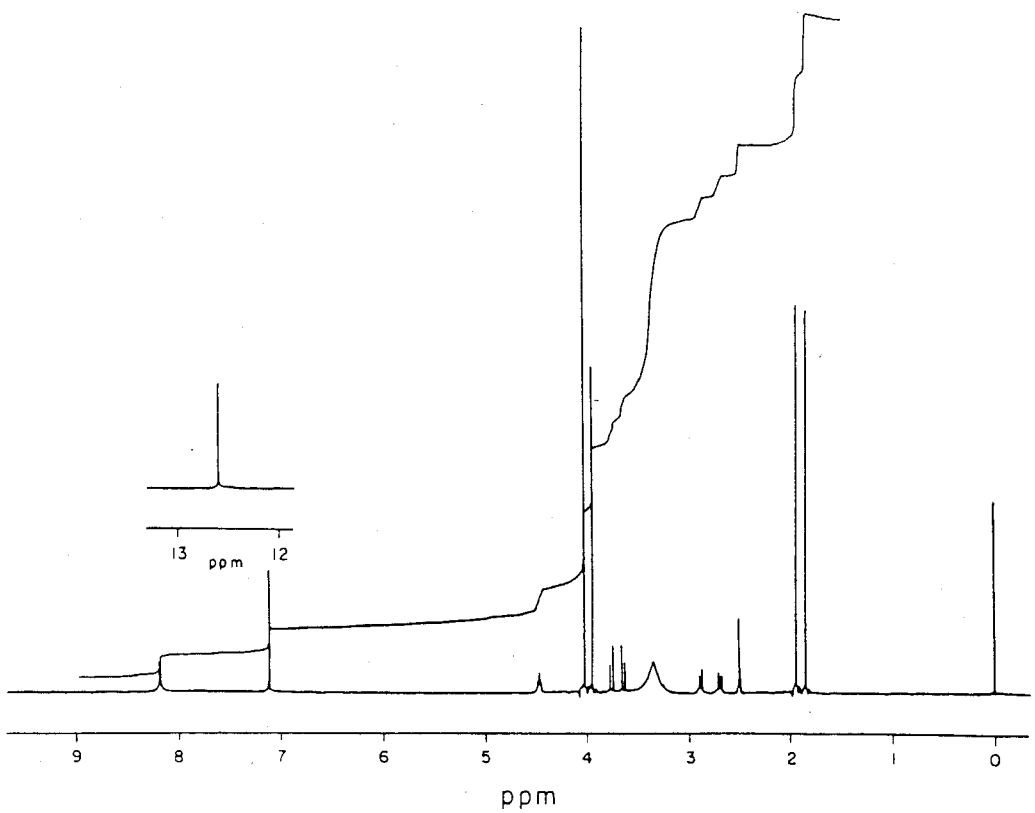
Figure 15:
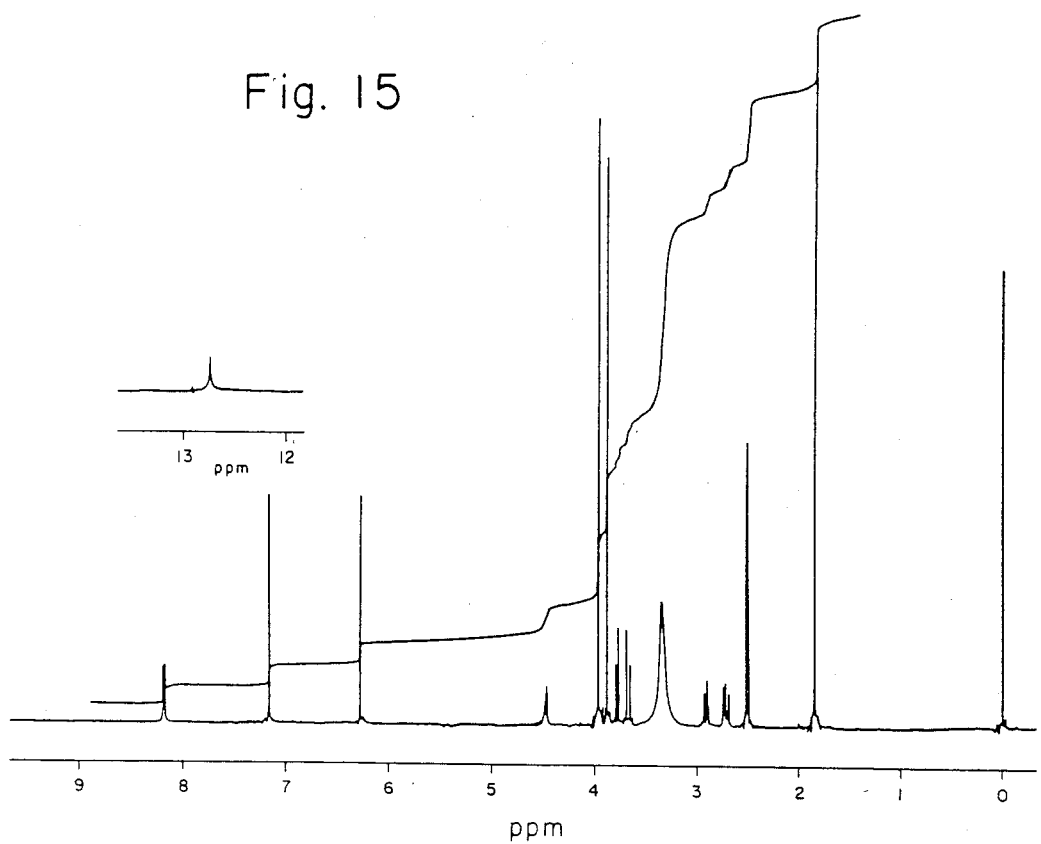
Figure 16:
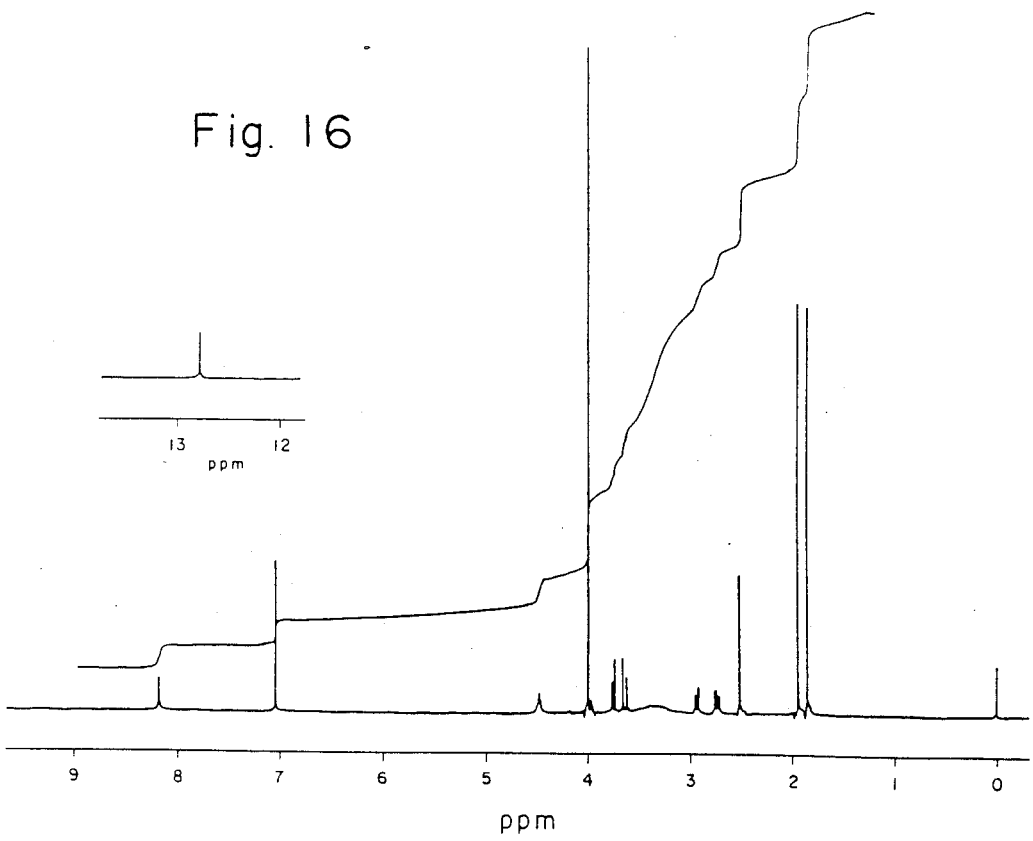
Figure 17:
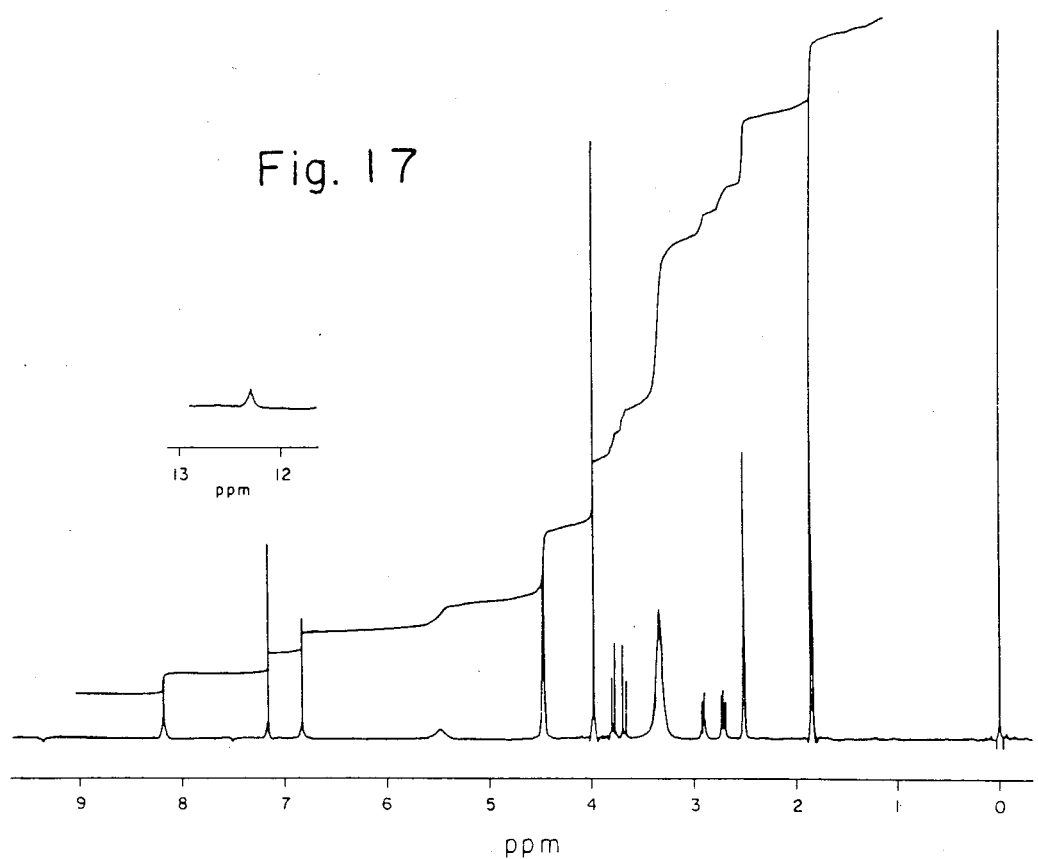
Figure 18:
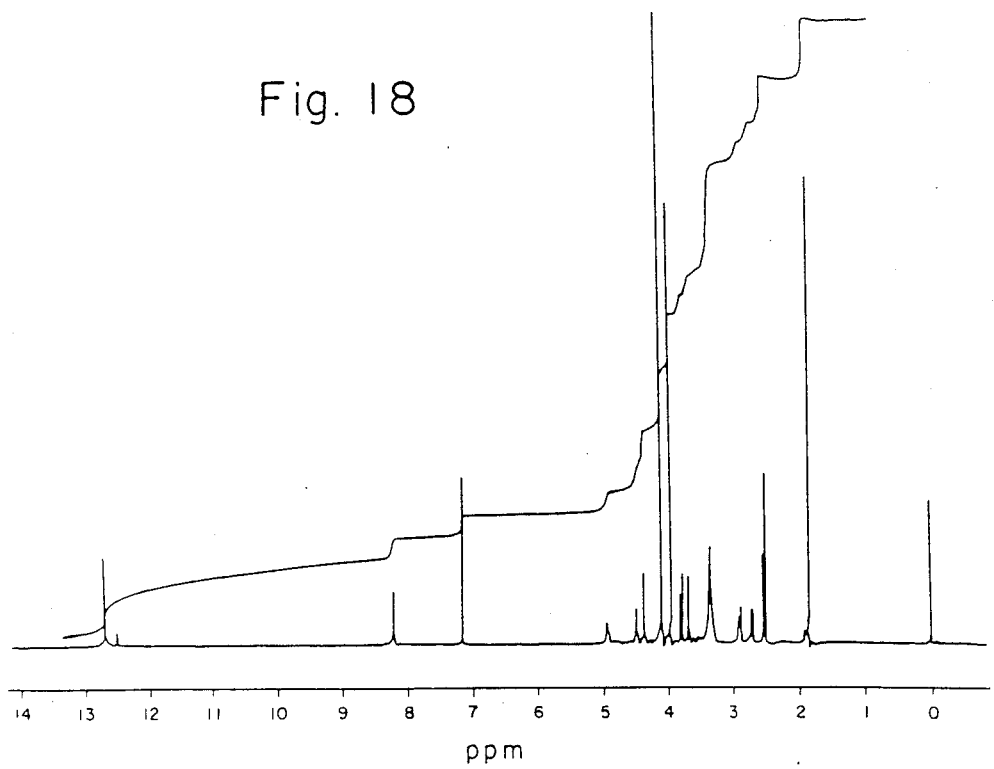
Figure 19:
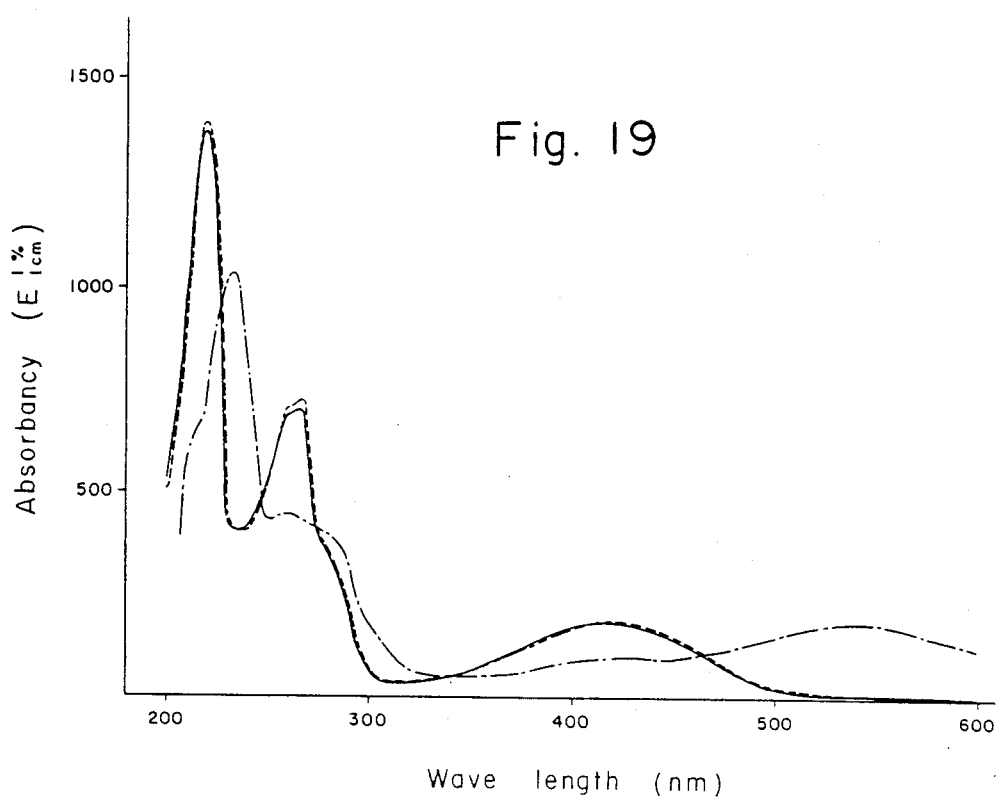
Figure 20:
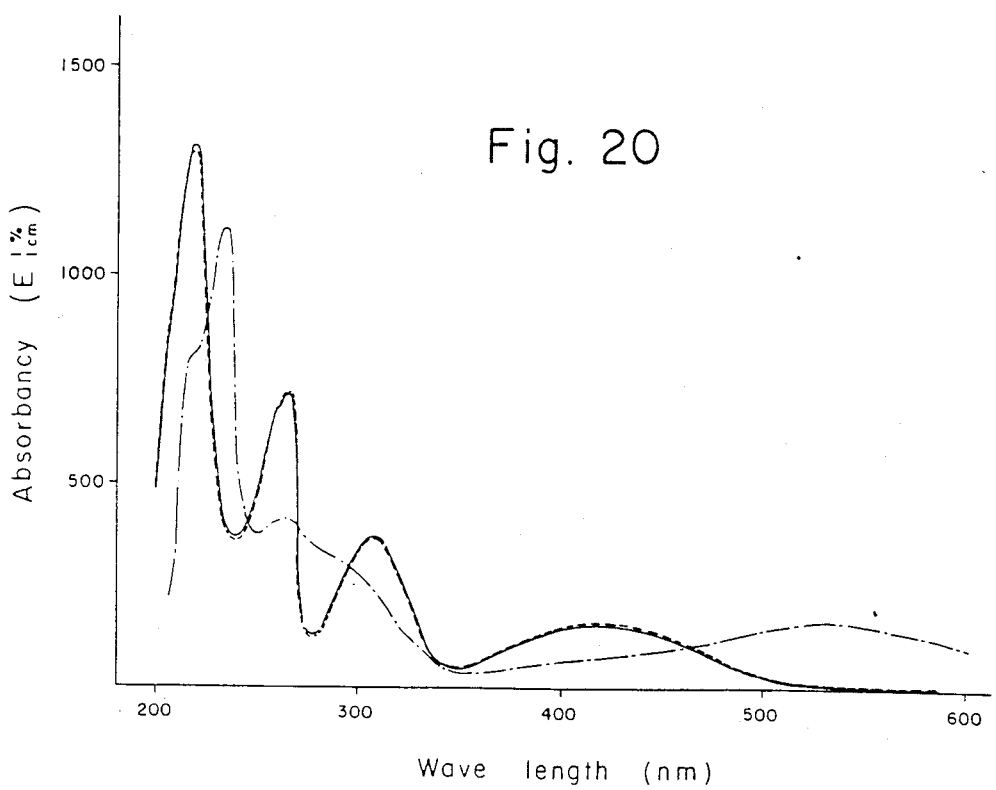
Figure 21:
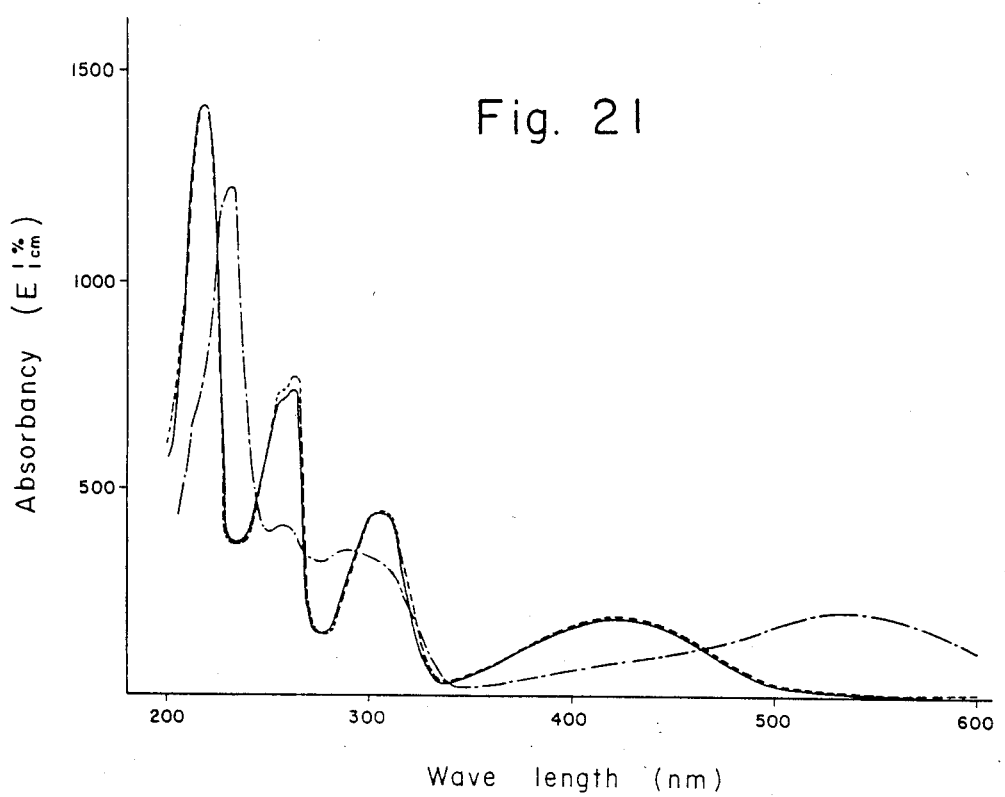
Figure 22:
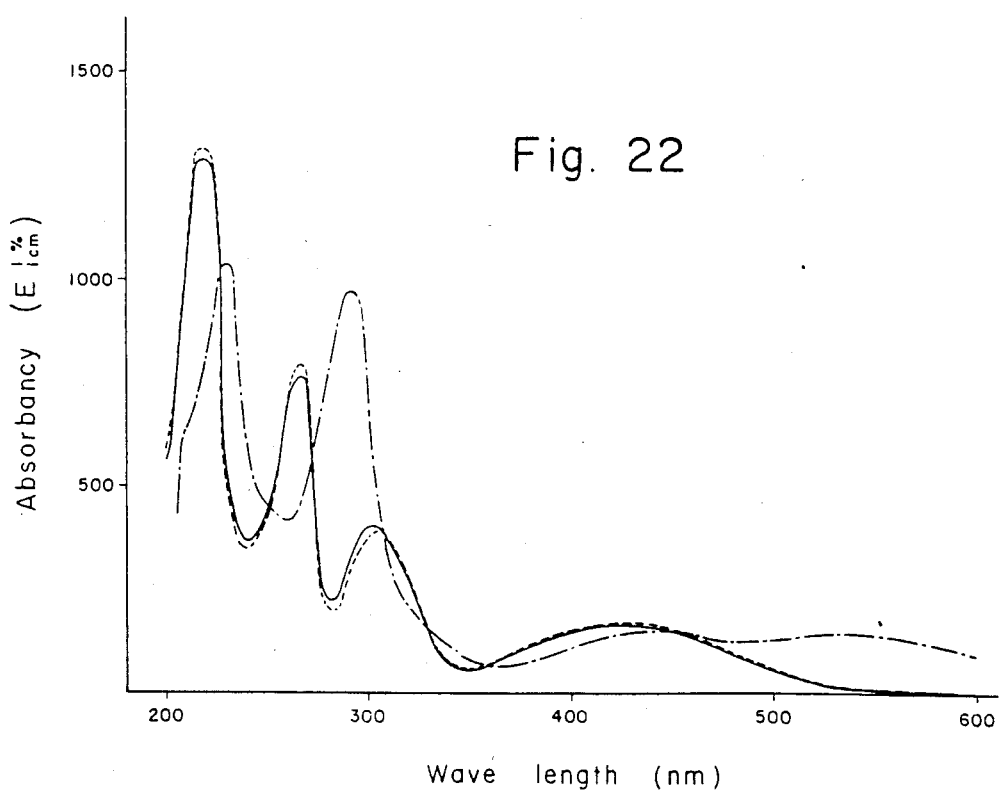
Figure 23:
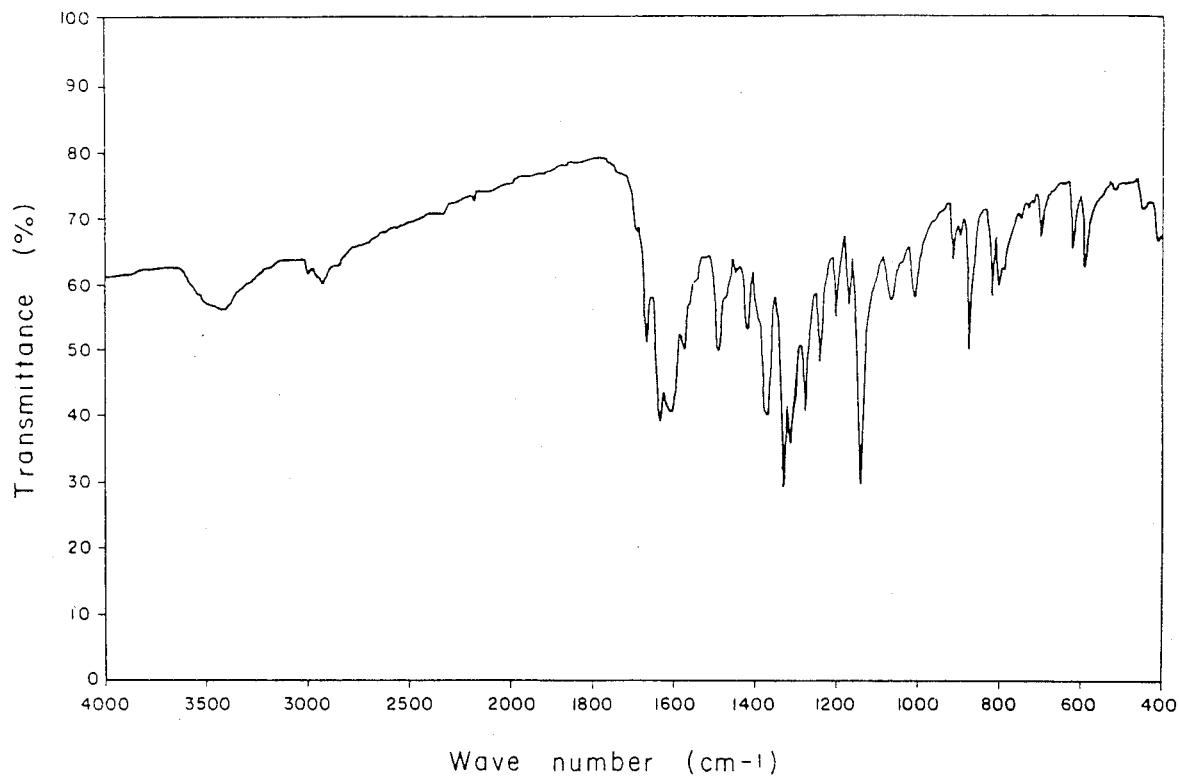
Figure 24:
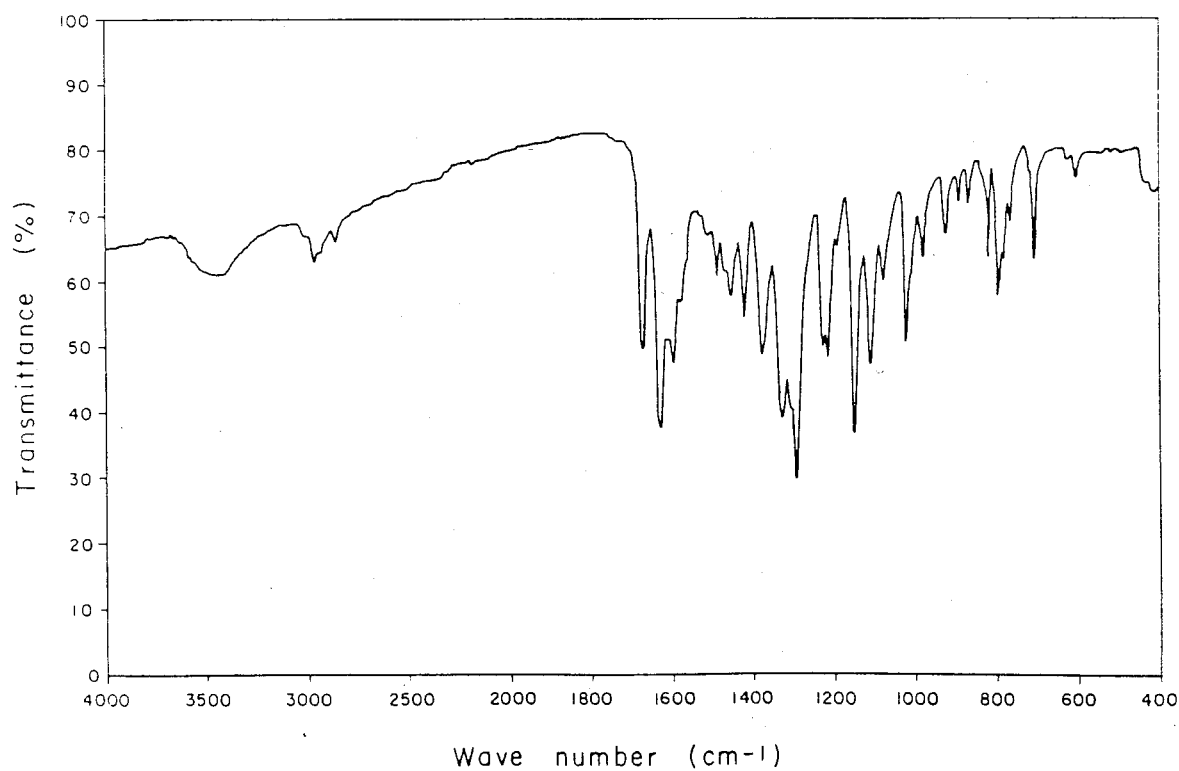
Figure 25:
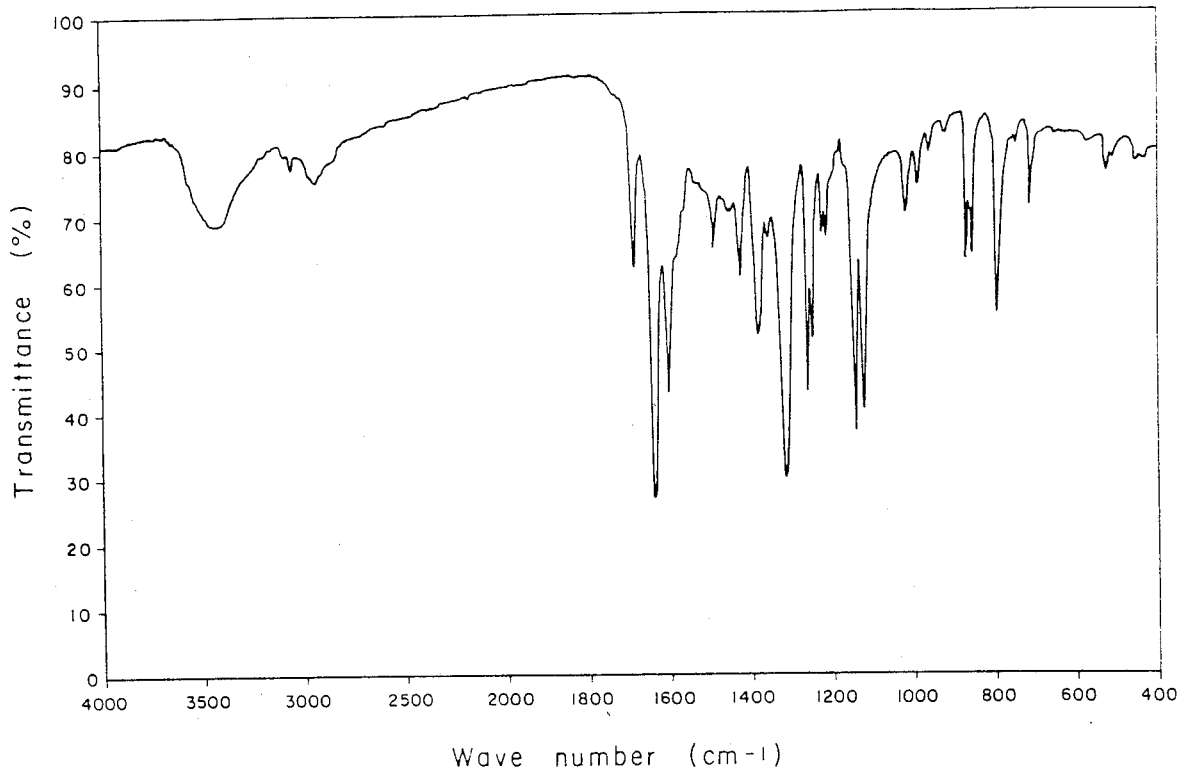
Figure 26:
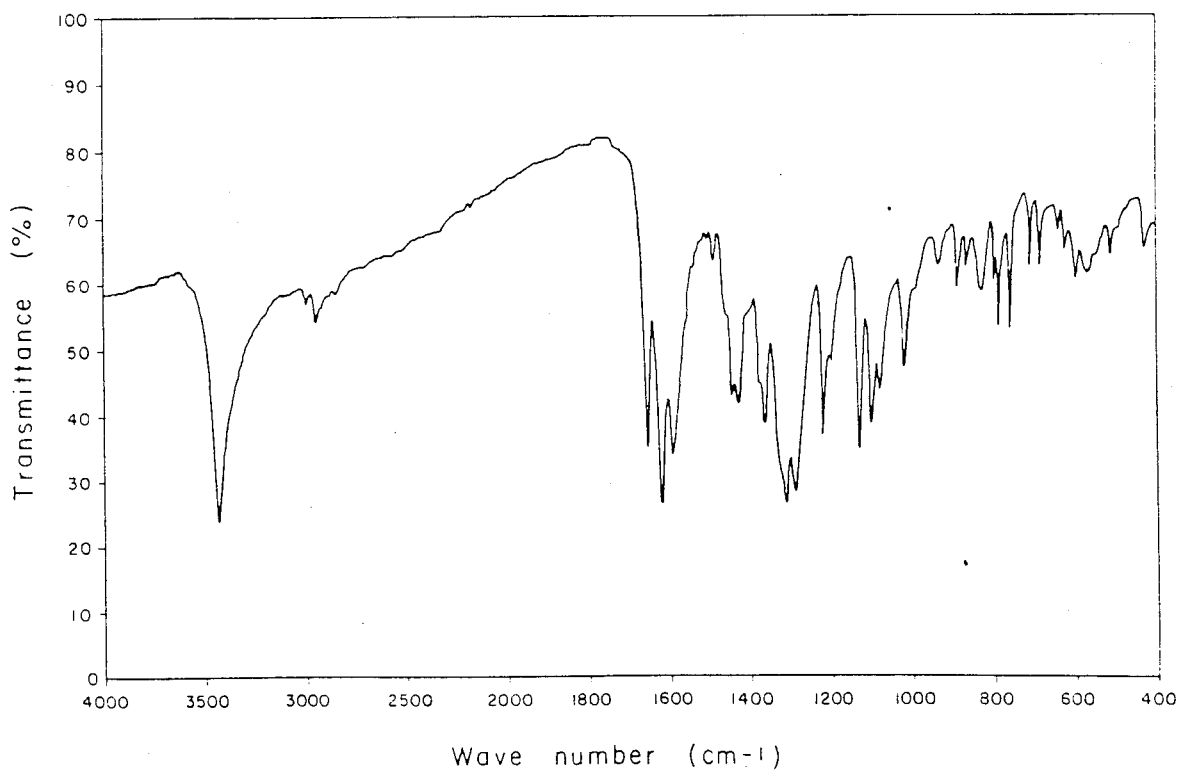
Figure 27:
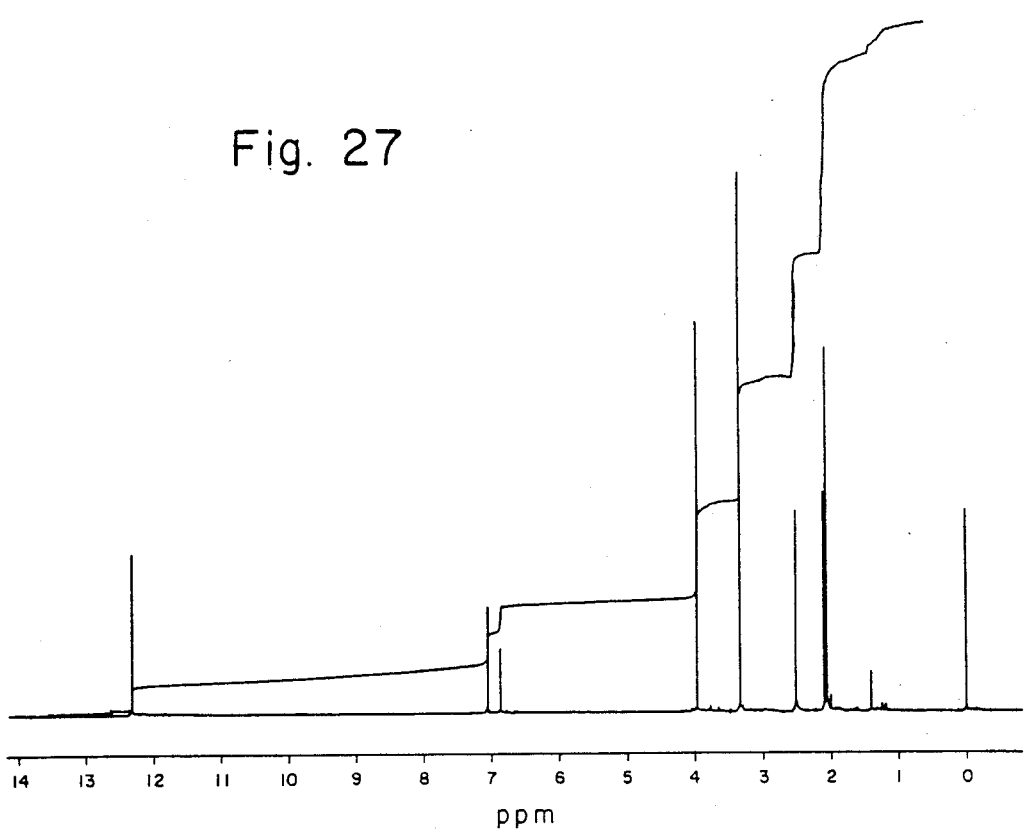
Figure 28:
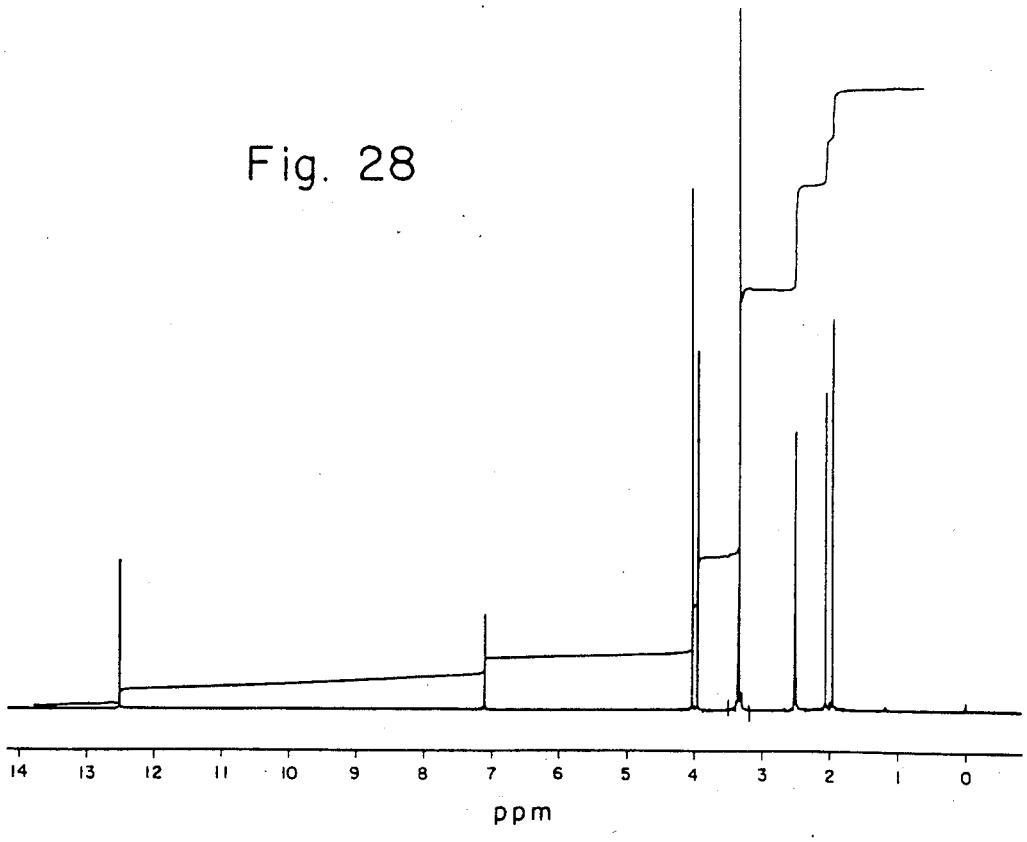
Figure 29:
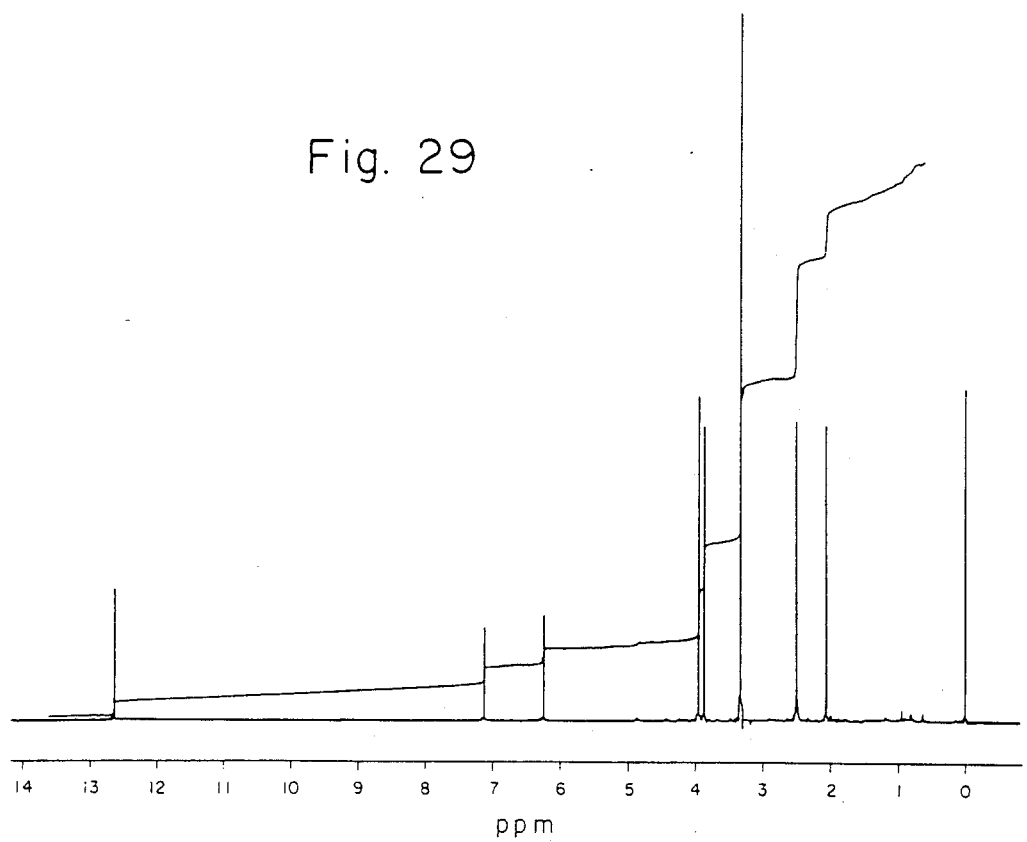
Figure 30:
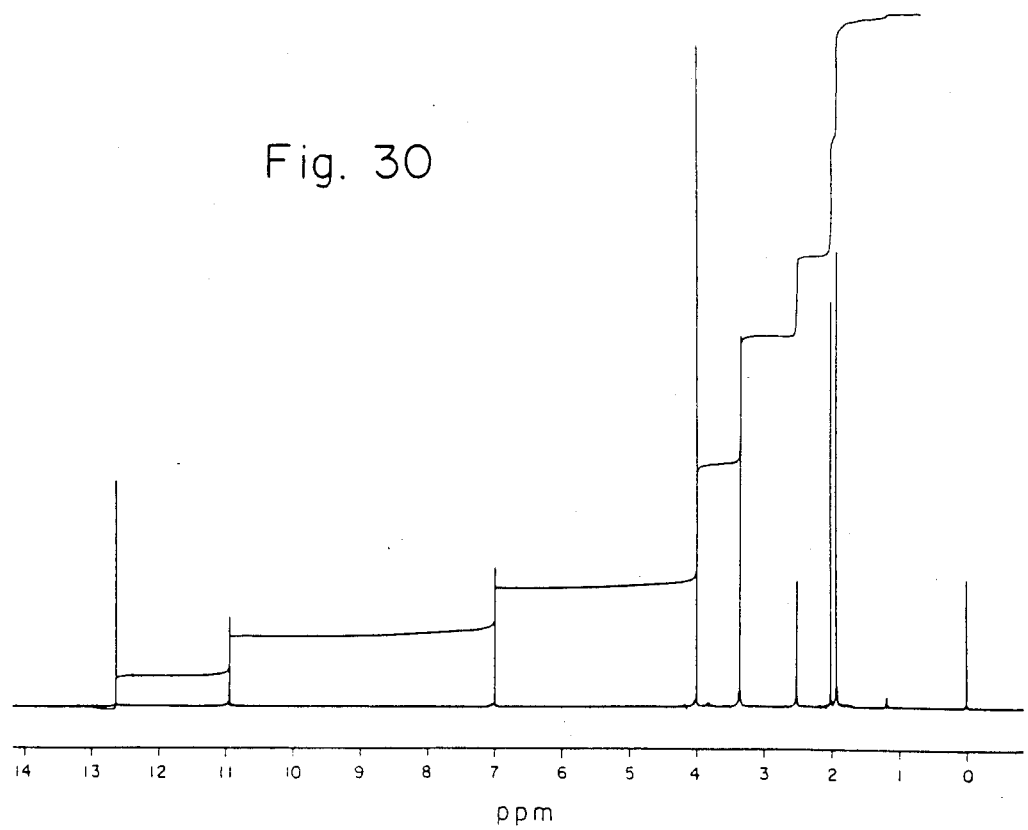

The following examples are further illustrative of the present invention. In the description referring to culture media, all percents are weight/volume percents.

EXAMPLE 1

A culture of Streptomyces sp. No. 23924 (IFO 14205, FERM BP-338) was used for inoculation of 400 ml of a liquid medium containing 2.0% glucose, 1.0% glycerin, 0.5% raw soybean meal, 0.5% corn steep liquor, 0.3% Polypepton (Daigo Nutritive Chemicals, Japan), 0.3% sodium chloride and 0.5% calcium carbonate in each of five 2-liter Sakaguchi flasks. Cultivation at 28° C. on a reciprocal shaker for 2 days gave about 2 liters of a culture broth. This culture broth was transferred to a 200-liter tank containing 100 liters of the same medium as above and cultivated at 28° C. for 2 days under aeration and agitation. Sixty liters of the culture broth thus obtained was transferred to a 2000-liter fermentation tank containing 1200 liters of a liquid medium containing 4% soluble starch, 2% defatted soybean meal, 0.1% sodium thiosulfate, 0.05% magnesium sulfate, 0.05% dipotassium hydrogen phosphate and 0.03% potassium chloride (pH 6.0) and cultured at 24° C. for 5 days under aeration and agitation. To 1150 liters of the fermentation broth thus obtained was added 15 kg of Topco Perlite #34 (Toko Perlite Kogyo, Japan) and the mixture was filtered with a filter press precoated with 34 kg of Hyflo-Supercel (Johns-Manville Products, U.S.A.) to remove mycelia and solid materials. About 1000 liters of a filtrate was obtained. The mycelia and solid materials was washed with 150 liters of water and filtered again to give about 150 liters of the washings. The filtrate and washings were combined, adjusted to pH 3.0 with sulfuric acid and sujbected to counter-current extraction in a Podbielniak Extractor Model 6150 (Podbielniak, U.S.A.) using ½ volume of ethyl acetate. The resulting extract, about 430 liters, was reextracted with ½ volume of 1% aqueous sodium hydrogen carbonate, whereby 215 liters of an extract was obtained. This extract was adjusted to pH 3.0 with sulfuric acid, extracted again with ½ volume of ethyl acetate, washed twice with ½ volume of water and concentrated under reduced pressure. The concentrate, 400 ml, was passed through a silica gel (Merck, West Germany) column (4.6×65 cm), and after passage of 500 ml of ethyl acetate, elution was carried out with 3 liters of 1% oxalic acid-ethyl acetate. The active fractions, about 3 liters, were pooled, washed with two 500-ml portions of water and concentrated to dryness under reduced pressure. The solid residue was dissolved in about 300 ml of dimethyl sulfoxide. The solution was diluted with 30 ml of water and introduced into a preparative liquid chromatograph (Waters Associates, U.S.A.), the Prep LC/System 500A fitted with a Prep PAK-500/$C_{18}$ column. Elution was carried out with 3 liters of methanol-water (1:1), 5 liters of methanol-water (3:2) and 2 liters of methanol in the order mentioned. The eluate was collected in 500-ml fractions. There were obtained fractions rich in P-23924A, C, D and E (Fractions 2–8, 3.5 liters) and fractions rich in P-23924B (Fractions 9–13; 2.5 liters). On standing at room temperature, the P-23924 B-containing fractions yielded orange-yellow crystals (about 2.3 g) of P-23924B. These crystals were separated by filtration and the mother liquor was concentrated under reduced pressure to about 1 liter. The concentrate was extracted with three ⅓-volume portions of ethyl acetate and the combined extract was dried over 50 g of anhydrous sodium sulfate and concentrated to about 30 ml. To the concentrate was added 200 ml of n-hexane, whereupon a crude orange-yellow crystalline powder (about 7.1 g) of P-23924B was obtained. The crude powder was recrystallized from methanol to give about 3 g of crystals of P-23924B. The fractions rich in P-23924A, C, D and E were concentrated to about 100 ml, chromatographed on a silica gel column (4.0×42 cm) and eluted with 2 liters of 1% oxalic acid-ethyl acetate. The eluate was collected in 100-ml fractions, whereby fractions rich in P-23924A and D (Fractions 2–7; 600 ml) and fractions rich in P-23924C and E (Fractions 8–14; 700 ml) were recovered. The former fractions (600 ml) were washed with water and concentrated to dryness. The solid residue was dissolved in 50 ml of methanol. The solution was diluted with 50 ml of water and introduced into the same preparative liquid chromatograph as above. Elution was carried out with 5.5 liters of methanol-water (1:1). The eluate was collected in 500-ml fractions, and 3 fractions (1.5 liters)

from Fractions 13 to 15 were combined and concentrated to about 700 ml under reduced pressure. The concentrate was extracted with three 200-ml portions of ethyl acetate and the combined extract was dehydrated over 30 g of anhydrous sodium sulfate and concentrated to about 30 ml under reduced pressure. To concentrate was added 200 ml of n-hexane, whereupon a crude orange-yellow powder (1.7 g) containing P-23924A and D was obtained. The crude powder was dissolved in 100 ml of chloroform-acetic acid (4:1) and chromatographed on a silica gel column (3.5×52 cm). Elution was carried out with 400 ml of chloroform-acetic acid (4:1) and 1 liter of chloroform-acetic acid (7:3). The eluate was collected in 10-ml fractions, whereby fractions rich in P-23924A (Fractions 25–29) and fractions rich in P-23924D (Fractions 36–136) were obtained. The former fractions (50 ml) were concentrated to dryness under reduced pressure and dissolved in 200 ml of methanol. The solution was diluted with 200 ml of water and again subjected to chromatography using the same preparative liquid chromatograph as above. Fractions rich in P-23924A were collected and concentrated under reduced pressure, extracted with ethyl acetate and, after dehydration, concentrated to give a crude powder (about 250 mg) of P-23924A. The crude powder was recrystalized from methanol to give orange-yellow crystals (about 100 mg) of P-23924A. The fractions (1 liter) rich in P-23924D were concentrated to dryness under reduced pressure and the solid residue was dissolved in about 500 ml of ethyl acetate. The solution was washed with three 200-ml portions of water. The ethyl acetate layer was dried over 50 g of anhydrous sodium sulfate and the solvent was distilled off under reduced pressure. To the resulting concentrate (about 30 ml) was added 200 ml of n-hexane, whereupon a crude powder (about 0.7 g) of P-23924D was obtained. The crude powder was dissolved in 25 ml of chloroform-acetic acid (4:1) and chromatographed on a silica gel column (3×45 cm). Elution was carried out with chloroform-acetic acid (4:1). The fractions with in P-23924D thus collected (400 ml) were concentrated to 80 ml under reduced pressure and the concentrate was diluted with 100 ml of water and extracted with three ½-volume portions of ethyl acetate. The combined extract was washed with water, dehydrated and deprived of the ethyl acetate. The thus-obtained crude powder (about 500 mg) was rrecrystallized from methanol-acetic acid (1:5) to yield a crystalline orange-yellow powder (about 330 mg) of P-23924D. On the other hand, fractions rich in P-23924C and E (Fractions 8–14; 700 ml) collected by the above silica gel chromatography were washed with water and dehydrated, and the ethyl acetate was distilled off. The residue was dissolved in 50 ml of methanol. The solution was diluted 2 times with water and introduced into a preparative liquid chromatograph (the same column as above). Elution was carried out with methanol-water (1:1). The eluate was collected in 200-ml fractions. There were obtained fractions rich in P-23924E (Fractions 10–13; 800 ml) and fractions rich in P-23924C (Fractions 14–18; 1 liter). The fractions rich in P-23924E were concentrated under reduced pressure, extracted with three ½-volume portions of ethyl acetate and, after dehydration, concentrated to about 20 ml. To the concentrate was added 200 ml of n-hexane, whereupon a crude orange-yellow powder (about 120 mg) of P-23924E was obtained. The crude powder was dissolved in 30 ml of chloroform-methanol (3:2) and chromatographed on a silica gel column (3×45 cm). Elution was carried out with chloroform-methanol (3:2). The thus-obtained fractions rich in P-23924E were concentrated to 10 ml. To the concentrate were added 10 ml of ethyl acetate and 50 ml of n-hexane, whereupon a crystalline orange-yellow powder (about 30 mg) of P-23924E was obtained. The fractions (1 liter) rich in P-23924C were concentrated to dryness under reduced pressure and the solid residue was dissolved in 15 ml of chloroform and chromatographed on a silica gel column (3.0×45 cm). Elution was carried out with chloroform-acetic acid (4:1) to recover fractions rich in P-23924C. The fractions were concentrated to dryness, whereupon a crude powder (about 150 mg) of P-23924C was obtained. The crude powder was dissolved in 70 ml of ethyl acetate, and the solution was washed with three 20-ml portions of water and dehydrated over 2.5 g of anhydrous sodium sulfate. The ethyl acetate solution was concentrated to about 10 ml under reduced pressure. To the concentrate was added 25 ml of n-hexane, whereupon orange-yellow crystals (about 85 mg) of P-23924C were obtained.

In the manner of the above, i.e. the procedures of extraction of the cultured broth with ethyl acetate, reextraction with 1% aqueous sodium hydrogen carbonate, extraction with ethyl acetate in acidic, washing with water and concentration, there was obtained 200 ml of a concentrate.

The concentrate was passed through a silica gel (Merck, West Germany) column (4.6×65 cm), and elution was carried out with 2 liters of ethyl acetate and then with 7 liters of ethyl acetate containing 1% oxalic acid. The active fractions, 2 liters, containing mainly P-23924F were collected, washed twice with 300 ml of water and then concentrated under reduced pressure to give solid residue. The solid residue was dissolved in 80 ml of chloroform-acetic acid (9:1). The solution was passed through a silica gel column (3.4×54 cm), and elution was carried out with 1.2 liter of chloroform-acetic acid (9:1), 1.2 liters of chloroform-acetic acid (8:2) and 1.2 liters of chloroform-acetic acid (7:3) in that order. The active fractions, about 1.5 liters, containing mainly P-23924F were collected, concentrated under reduced pressure to give solid residue. The solid residue was dissolved in 400 ml of methanol-water (1:1) and then thus obtained solution was introduced into a preparative liquid chromatography, the Prep LC/System 500A fitted with a Prep PAK-500/$C_{18}$ column. Elution was carried out with 5 liters of methanol-water (3:2). The fractions mainly containing P-23924F were collected, and concentrated under reduced pressure to give 1.3 g of crude powder of P-23924F. The crude powder was subjected to recrystallization with methanol-water (8:2), whereby about 500 mg of yellow-orange crystals of P-23924F was obtained.

EXAMPLE 2

Sixty (60) liters of a seed culture obtained in the manner of Example 1 was transferred into a 2000-liter fermentation tank containing 1200 liters of a liquid medium composed of 4% soluble starch, 1% dextrin, 2% defatted soybean meal, 0.1% sodium thiosulfate, 0.05% ferrous sulfate heptahydrate, 0.05% dipotassium hydrogen phosphate and 0.03% potassium chloride (pH 6.0) and cultivated at 24° C. for 6 days under aeration and agitation. The culture broth (about 1100 liters) was filtered, extracted with ethyl acetate, reextracted with sodium hydrogen carbonate and again extracted with ethyl acetate in the manner of Example 1. This extract was concentrated to 700 ml. The concentrate was chromatographed on a silica gel column (5.4×65 cm). After passage of 3 liters of ethyl acetate, elution was carried out with 10 liters of 1% oxalic acid-ethyl acetate. Eluate fractions rich in P-23924A, B and D (2.6 liters) and fractions rich in P-23924C, E (4.2 liters) and F (3.0 liters) were recovered. The former fractions were washed with water and, after dehydration, the ethyl acetate was distilled off. The residue was dissolved in 200 ml of methanol. To the resulting solution were added 200 ml of dimethyl sulfoxide and 200 ml of water. This solution was introduced into a preparative liquid chromatograph, the Prep LC/system 500A fitted with a Prep PAK-500/$C_{18}$ column. Elution was carried out with methanol-water (1:1). Eluate fractions rich in P-23924A and D (2.5 liters) and fractions rich in P-23924B (3.1 liters) were thus recovered. The former fractions were again subjected to chromatography using the same liquid chromatograph as above. The fractions thus obtained were concentrated and extracted with ethyl acetate. This extract was dehydrated and concentrated to 50 ml. The concentrate was passed through a silica gel column (4.5×70 cm), elution being carried out with 1.5 liters of dichloromethane-acetic acid (9:1), 5.0 liters of dichloromethane-acetic acid (8:2) and 2 liters of dichloromethane-acetic acid (7:3) in that order. There were collected eluate fractions (1 liter) rich in P-23924A and fractions (1.2 liters) rich in P-23924D. The former fractions were washed with three 300-ml portions of water and the dichloromethane layer was concentrated to dryness. The solid residue was dissolved in 200 ml of methanol and diluted with 200 ml of water. The dilution was subjected to preparative liquid chromatography under the same conditions as above. Fractions rich in P-23924A were recovered, concentrated to remove the methanol and extracted with three ⅓-volume portions of ethyl acetate. The extracts were combined, dehydrated and concentrated to dryness. The residue was dissolved in methanol. On standing, the solution yielded crystals of P-23924A (300 mg). The P-23924D-containing solution (1.2 liters) was concentrated under reduced pressure. The concentrate, 30 ml, was chromatographed on a silica gel column (3.5×50 cm) and eluted with 1 liter each of dichloromethane-acetic acid mixtures (9:1, 8:2 and 7:3) in that order. The fractions rich in P-23924D (1.4 liters) recovered were concentrated to dryness under reduced pressure. The solid residue was dissolved in 200 ml of methanol and diluted with 200 ml of water. The dilution was subjected to preparative liquid chromatography under the same conditions as above and fractions rich in P-23924D (2.7 liters) were recovered. The methanol was distilled off under reduced pressure. The concentrate (1.5 liters) was extracted with three ⅓-volume portions of ethyl acetate. The extract was dehydrated and concentrated to about 25 ml. On standing, the concentrate yielded crystals of P-23924D (about 1 g). The P-23924B-containing fractions (3.1 liters), on standing at room temperature, yielded crystals of P-23924B. These crystals were recovered and recrystallized from methanol to give crystals of P-23924B (about 3 g). The aforementioned P-23924C- and E-containing fractinos (4.2 liters) was washed three times with 1 liter of water and dehydrated over 30 g of anhydrous sodium sulfate, and the ethyl acetate was distilled off. The residue was dissolved in 200 ml of methanol and diluted with 200 ml of water. The dilution was subjected to liquid chromatography under the same conditions as above, and fractions rich in P-23924E (1.8 liters) and fractions rich in P-23924C (2.4 liters) were recovered. The P-23924E-containing fractions (1.8 liters) were concentrated to about 50 ml under reduced pressure. The concentrate was chromatographed on a Sephadex LH-20 (Pharmacia, Sweden) column (3.5×52 cm) (packed as a suspension in methanol) and eluted with methanol. Fractions containing P-23924E alone (200 ml) were combined and concentrated to 20 ml under reduced pressure. To the concentrate were added 20 ml of ethyl acetate and 200 ml of n-hexane, whereupon an orange-yellow crystalline powder of P-23924E (about 700 mg) was obtained. The P-23924C-containing fractions (2.4 liters) were concentrated under reduced pressure. The concentrate (1.2 liters) was extracted with three ⅓-volume portions of ethyl acetate, and the ethyl acetate layer was dehydrated over 20 g of anhydrous sodium sulfate and, then, the ethyl acetate was distilled off. The residue was dissolved in methanol. The resulting solution, on standing, yielded crude crystals of P-23924C. The crude crystals were recrystallized from methanol to give crystals of P-23924C (1.5 g).

The above active fractions, 3.0 liters, containing mainly P-23924F was washed with water and dried over. Ethyl acetate was evaporated, and thus obtained residue was dissolved in 100 ml of chloroform-acetic acid (9:1). The solution was passed through a silica gel column (3.4×54 cm), and elution was carried out with 1 liter of chloroform-acetic acid (9:1), 1 liter of chloroform-acetic acid (8:2) and 1 liter of chloroform-acetic acid (7:3).

The active fractions, 1.8 liters, containing mainly P-23924F were collected and concentrated to dryness. The dried resultant was dissolved in 400 ml of methanol-water (1:1). Thus obtained solution was introduced into a preparative liquid chlomatograph, the Prep LC/System 500A fitted with a Prep PAK-500/$C_{18}$ column. Elution was carried out with 3.0 liters of methanol-water (3:2). The active fractions, 2.4 liters, containing mainly P-23924F were collected, and concentrated, whereupon crude crystals of P-23924F were precipitated. Recrystallization of the crude crystals with methanol-water (3:2) gave 2.5 g of crystals of P-23924F.

EXAMPLE 3

In 300 ml fo methanol was dissolved 1 g of P-23924A, and the solution is subjected to catalytic reduction with 5 g of Raney nickel under the initial pressure of 100 Kg/$cm^2$ and at reaction temperature 70° C. for 5 hours. Thus obtained reaction mixture was subjected to filtration to remove the catalyst, and the filtrate was concentrated to 20 ml under reduced pressure. The concentrate was diluted with water to give a 300 ml solution. The solution was extracted three times with 100 ml each portion of ethyl acetate, the extracts were combined and washed twice with 50 ml of water, the ethyl acetate layers were separated, dried and concentrated under reduced prressure to give 119 mg of orange red crystals of P-23924AR.

EXAMPLE 4

In 500 ml of methanol was dissolved 2.5 g of P-23924B, and the solution is subjected to catalytic reduction with 15 g of Raney nickel under the initial pressure of 100 Kg/$cm^2$ and at the reaction temperature 70° C. for 5 hours. Thus obtained reaction mixture was subjected to filtration to remove the catalyst, and the filtrate was concentrated to dryness under reduced pressure. The residue was dissolved in 250 ml of ethyl acetate. The solution was washed three times with 100 ml each portion of water, the ethyl acetate layers were separated, dried and concentrated under reduced pressure to give whereby 0.9 g of orange red crystals of P-23924BR.

EXAMPLE 5

In 700 ml of methanol was dissolved 3 g of P-23924C, and the solution is subjected to catalytic reduction with 15 g of Raney nickel under the initial pressure of 100 Kg/cm$^2$ and at reaction temperature 70° C. for 5 hours. Thus obtained reaction mixture was subjected to filtration to remove the catalyst, and the filtrate was concentrated under reduced pressure to dryness. The residue was dissolved in 800 ml of ethyl acetate. The solution was washed three times with 300 ml each portion of water, the ethyl acetate layers were separated, dried and concentrated under reduced pressure to give whereby 1.23 g of orange red crystals of P-23924CR.

EXAMPLE 6

One gram of P-23924 D was treated with the manner of Example 3, whereupon 341 mg of orange red cyrstals of P-23924 DR was obtained.

EXAMPLE 7

| Tablet | |
| --- | --- |
| (1) P-23924A, B, E or F | 100 mg |
| (2) Lactose | 47 mg |
| (3) Corn starch | 40 mg |
| (4) Hydroxypropylcellulose-L | 12 mg |
| (5) Magnesium stearate | 1 mg |
| | 200 mg/tablet |

A mixture of the above ingredients is tableted by the conventional method (wet method).

EXAMPLE 8

| Capsule | |
| --- | --- |
| (1) P-23924C | 100 mg |
| (2) Lactose | 135 mg |
| (3) Corn starch | 60 mg |
| (4) Magnesium stearate | 5 mg |
| | 300 mg/capsule |

The above ingredients (1), (2), (3) and (4) (half the above amount) are mixed and granulated by the conventional method. To the granules is added the remaining amount of the ingredient (4). The mixture is packed into a gelatin capsule No. 1 (according to the Pharmacopoeia of Japan, Tenth Edition).

EXAMPLE 9

| Capsule | |
| --- | --- |
| (1) P-23924D | 300 mg |
| (2) Lactose | 135 mg |
| (3) Corn starch | 60 mg |
| (4) Magnesium stearate | 5 mg |
| | 500 mg/capsule |

The above ingredients (1), (2), (3) and (4) (half the above amount) are mixed and granulated by the conventional method. To the granules is added the remaining amount of the ingredient (4). The mixture is packed into a gelatin capsule No. 00 (according to the Pharmacopoeia of Japan, Tenth Edition).

EXAMPLE 10

| Tablet | |
| --- | --- |
| (1) P-23924 AR, BR, CR or DR | 100 mg |
| (2) Lactose | 47 mg |
| (3) Corn starch | 40 mg |
| (4) Hydroxypropylcellulose-L | 12 mg |
| (5) Magnesium stearate | 1 mg |
| | 200 mg/tablet |

A mixture of the above ingredients is tableted by the conventional method (wet method).

What we claim is:

1. A compound represented by the formula:

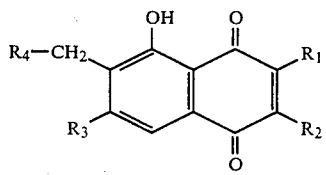

wherein $R_1$ is hydrogen, methyl or hydroxymethyl, $R_2$ is hydrogen or methoxy, $R_3$ is hydroxy or methoxy and $R_4$ is hydrogen or a group

2. A compound as claimed in claim 1, wherein $R_4$ is a group

3. A compound as claimed in claim 1, wherein $R_4$ is hydrogen.

4. A compound as claimed in claim 1, wherein $R_1$ is methyl, $R_2$ is hydrogen, $R_3$ is methoxy and $R_4$ is a group

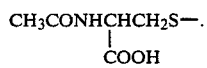

5. A compound as claimed in claim 1, wherein $R_1$ is methyl, $R_2$ is methoxy, $R_3$ is methoxy and $R_4$ is a group

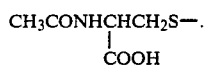

6. A compound as claimed in claim 1, wherein $R_1$ is hydrogen, $R_2$ is methoxy, $R_3$ is methoxy and $R_4$ is a group

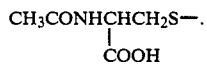

7. A compound as claimed in claim 1, wherein $R_1$ is methyl, $R_2$ is methoxy, $R_3$ is hydroxy and $R_4$ is a group

8. A compound as claimed in claim 1, wherein $R_1$ is hydroxymethyl, $R_2$ is hydrogen, $R_3$ is methoxy and $R_4$ is a group

9. A compound as claimed in claim 1, wherein $R_1$ is hydroxymethyl, $R_2$ is methoxy, $R_3$ is methoxy and $R_4$ is a group

10. A compound as claimed in claim 1, wherein $R_1$ is methyl, $R_2$ is hydrogen, $R_3$ is methoxy and $R_4$ is hydrogen.

11. A compound as claimed in claim 1, wherein $R_1$ is methyl, $R_2$ is methoxy, $R_3$ is methoxy and $R_4$ is hydrogen.

12. A compound as claimed in claim 1, wherein $R_1$ is hydrogen, $R_2$ is methoxy, $R_3$ is methoxy and $R_4$ is hydrogen.

13. A compound as claimed in claim 1, wherein $R_1$ is methyl, $R_2$ is methoxy, $R_3$ is hydroxy and $R_4$ is hydrogen.

14. An antifibrotic preparation comprising an effective amount of at least one compound of claim 1 and a pharmaceutically acceptable carrier, excipient or diluent.